United States Patent [19]

Bargain et al.

[11] 4,275,184
[45] Jun. 23, 1981

[54] ETHYLENIC SILICON COMPOUNDS AND THERMOPLASTIC ELASTOMERS OBTAINED THEREFROM

[75] Inventors: Michel Bargain, Lyons; Marcel Lefort, Caluire, both of France

[73] Assignee: Rhone-Poulenc Industries, Paris, France

[21] Appl. No.: 88,584

[22] Filed: Oct. 26, 1979

Related U.S. Application Data

[62] Division of Ser. No. 965,529, Dec. 1, 1978, Pat. No. 4,213,914, which is a division of Ser. No. 851,898, Nov. 16, 1977, Pat. No. 4,147,711, which is a division of Ser. No. 617,513, Sep. 29, 1975, Pat. No. 4,088,670.

[30] Foreign Application Priority Data

Oct. 1, 1974 [FR] France ............... 74 33041
Feb. 11, 1975 [FR] France ............... 75 04191
Feb. 11, 1975 [FR] France ............... 75 04192

[51] Int. Cl.³ .................................. C08G 77/04
[52] U.S. Cl. ............................ 528/26; 528/28; 528/31; 528/32; 556/419; 556/422
[58] Field of Search ................ 528/26, 28, 31, 32; 556/422, 419

[56] References Cited

U.S. PATENT DOCUMENTS 4,088,670  5/1978  Bargain et al. ............ 556/422
4,145,508  3/1979  Bargain et al. ............ 528/32
4,147,711  4/1979  Bargain et al. ............ 556/442

Primary Examiner—Melvyn I. Marquis
Attorney, Agent, or Firm—Stevens, Davis, Miller & Mosher

[57] ABSTRACT

The invention provides organosilicon compounds of the formula:

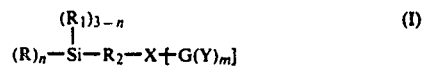

in which:
n is 1, 2 or 3;
each R, which may be identical or different, is a monovalent organic group which contains a carbon-carbon double bond and from 2 to 10 carbon atoms;
each $R_1$, which may be identical or different, is a straight or branched alkyl radical optionally substituted by one or more halogen atoms or cyano groups; an aryl radical or an alkylaryl radical optionally substituted by one or more halogen atoms;
$R_2$ is a straight or branched divalent alkylene or alkylidene radical possessing up to 4 carbon atoms;
X is a divalent radical consisting of, or containing, at least one hetero-atom selected from oxygen, sulphur and nitrogen atoms, the radical being attached to the radical $R_2$ via a said hetero-atom;
G is an organic radical of valency (m+1) possessing from 1 to 30 carbon atoms;
m is 1, 2 or 3;
and each Y, which may be identical or different, is a functional group selected from

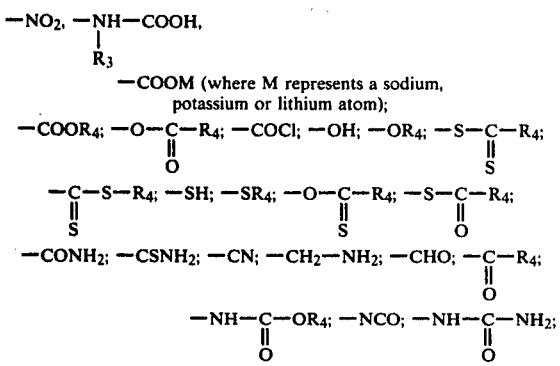

wherein $R_3$ represents a hydrogen atom or a straight or branched alkyl radical possessing up to 6 carbon atoms and $R_4$ represents an alkyl radical possessing up to 4 carbon atoms, with the proviso that two Y groups can together constitute an imide group

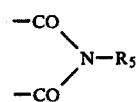

wherein $R_5$ represents a hydrogen atom or a straight or branched alkyl radical possessing up to 4 carbon atoms.

These are useful intermediates in the preparation of disilanes and silicon polymers, in particular of polyethylenic silicon compounds which can be polymerized with an α,ω-dihydrogenopolysiloxane to give thermoplastic elastomers.

57 Claims, No Drawings

ETHYLENIC SILICON COMPOUNDS AND THERMOPLASTIC ELASTOMERS OBTAINED THEREFROM

This is a division of application Ser. No. 965,529 filed Dec. 1, 1978, now U.S. Pat. No. 4,213,914 which in turn is a division of application which in turn is a Ser. No. 851,898, filed Nov. 16, 1977, now U.S. Pat. No. 4,147,711, granted Apr. 3, 1979, which in turn is a division of application Ser. No. 617,513, filed Sept. 29, 1975, now U.S. Pat. No. 4,088,670, granted May 9, 1978.

The present invention relates to ethylenic silicon compounds containing at least one functional group other than the ethylenic double bond, polyethylenic silicon compounds with carbo-functional units and thermoplastic elastomers with carbo-functional units obtained from the latter.

The value of silicon compounds containing at least two functional groups is well known because such compounds open the way to organo-silicon polymers and copolymers. Thus, bis-(carboxyphenyl)-dimethylsilane and bis-(carboxyphenyl)-tetramethyldisiloxane have been described. These compounds have been used to prepare polyamides and polyesters (see, for example, U.S. Pat. No. 2,754,284).

A. More specifically, a first subject of the present invention are the ethylenic compounds of the general formula:

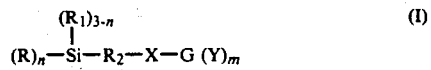

and the process by which they may be obtained.

In the formula (I) each symbol represents:

n: an integer which may have the value 1, 2 or 3.

R: identical or different monovalent organic groups which contain an ethylenic double bond and comprise from 2 to 10 carbon atoms.

$R_1$: identical or different straight or branched alkyl radicals optionally substituted by one or more halogen atoms or by one or more cyano groups; aryl radicals and alkylaryl radicals, these radicals being optionally substituted by one or more halogen atoms.

$R_2$: a straight or branched divalent alkylene or alkylidene radical possessing from 1 to 4 carbon atoms.

X: a divalent radical consisting of, or containing, at least one hetero-atom O, S or N, this radical X being attached to the radical $R_2$ via a said hetero-atom.

G: an organic radical of valency (m+1) possessing from 1 to 30 carbon atoms.

m: an integer which assumes the values 1, 2 and 3.

Y: identical or different functional groups chosen from the list of the following groups:

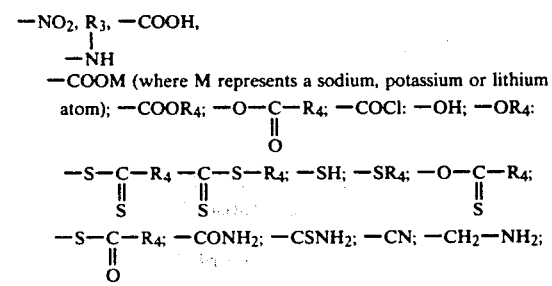

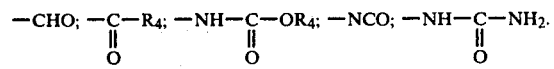

The radical $R_3$ represents a hydrogen atom or a straight or branched alkyl radical possessing from 1 to 6 carbon atoms and $R_4$ represents a straight or branched alkyl radical possessing from 1 to 4 carbon atoms. Furthermore, two groups Y can together constitute an imide group

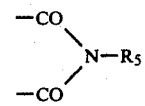

wherein $R_5$ represents a hydrogen atom or a straight or branched alkyl radical having from 1 to 4 carbon atoms.

More precisely, the various preceding symbols suitably assume the following meanings:

I-RADICAL R

This radical represents a straight or branched alkenyl group optionally substituted by one or more halogen atoms, or a cycloalkenyl group optionally substituted by one or more halogen atoms. In this context there may be mentioned straight or branched alkenyl groups having from 2 to 6 carbon atoms and optionally substituted by one to three atoms of chlorine and/or of fluorine, such as the following groups: vinyl, allyl, 2,2-dichlorovinyl, 1,2,2-trichlorovinyl, prop-2-enyl, but-2-enyl, prop-1-enyl, but-1-enyl and 2-methyl-prop-1-enyl.

R can also represent a monovalent group of the formula

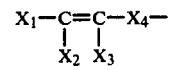

in which: the symbols $X_1$, $X_2$ and $X_3$ independently represents a hydrogen atom or a straight or branched alkyl group having from 1 to 4 carbon atoms, such as the methyl, ethyl and isobutyl radicals, or a phenyl group; $X_4$ denotes one of the following organo-silicon groups:

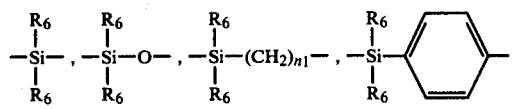

wherein the radicals $R_6$, which may be identical or different, represent a methyl or phenyl group and $n_1$ is an integer equal to 1, 2 or 3.

Preferably R represents a linear alkenyl group having from 2 to 6 carbon atoms.

II-RADICAL $R_1$

It represents, more specifically:

Straight or branched alkyl groups having at most 10 carbon atoms and optionally substituted by one to four atoms of chlorine and/or fluorine or by a cyano group, or aryl groups such as phenyl, or alkylaryl groups containing from 1 to 4 carbon atoms in the alkyl substituent, such as tolyl or xylyl radicals; these aromatic radicals are optionally substituted by one to four atoms of chlorine and/or fluorine.

Amongst these radicals there may be mentioned the following groups: methyl; ethyl; propyl; isopropyl; butyl; isobutyl; a-pentyl; t-butyl; chloromethyl; dichloromethyl; a-chloroethyl; a,β-dichloroethyl; fluoromethyl; difluoromethyl; a,β-difluoroethyl; 3,3,3-trifluoropropyl; 4,4,4-trifluorobutyl; 3,3,4,4,5,5-heptafluoropentyl; β-cyanoethyl; γ-cyanopropyl; phenyl; p-chlorophenyl; m-chlorophenyl; 3,5-dichlorophenyl; trichlorophenyl; tetrachlorophenyl; o-, p- or m-tolyl; a,a,a-trifluorotolyl; and xylyl groups such as 2,3-dimethylphenyl and 3,4-dimethylphenyl.

The radical $R_1$ preferentially represents an alkyl radical having from 1 to 5 carbon atoms optionally substituted by 1 to 4 atoms of chlorine and/or fluorine, or a phenyl radical.

III-RADICAL $R_2$

This radical represents a divalent radical defined above such as methylene, ethylene, trimethylene, ethylidene, tetramethylene, isopropylidene and methylethylene.

Preferably, $R_2$ represents a methylene or ethylene group.

IV-RADICAL X

This radical suitably represents one of the following groups linked by the hetero-atom to the radicals $R_2$:

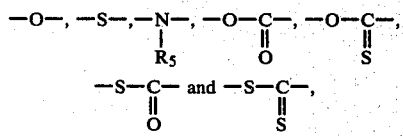

wherein $R_5$ has the meaning given above.

X preferentially represents an oxygen atom or sulphur atom or a

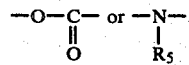

group (wherein $R_5$ represents a hydrogen atom or a methyl or ethyl radical).

V-RADICAL G

It suitably represents the following divalent, trivalent or tetravalent radicals:

1. A hydrocarbon radical which may be saturated or unsaturated, straight or branched, aliphatic or cycloaliphatic, optionally substituted by one or more chlorine atoms; a monocyclic or polycyclic aromatic radical optionally substituted by one or more methyl radicals and/or one or more chlorine atoms, it being possible for these aromatic radicals to form, with each other, ortho-condensed or ortho- and peri-condensed systems.

2. A saturated or unsaturated or aromatic, monocyclic or polycyclic heterocyclic radical containing at least one of the hetero-atoms, O, N and S, this heterocyclic radical optionally being substituted by methyl radicals.

The term "polycyclic heterocyclic radical" denotes a radical containing at least two heterocyclic structures or at least one heterocyclic structure combined with at least one aromatic or non-aromatic hydrocarbon ring, the whole forming an ortho-condensed or ortho- and peri-condensed system. This meaning is intended throughout this Specification.

3. A radical consisting of a chain of several divalent alkylene and/or cycloalkylene and/or arylene and/or heterocyclic radicals, linked to one another by a valency bond and/or by at least one of the following divalent groups:

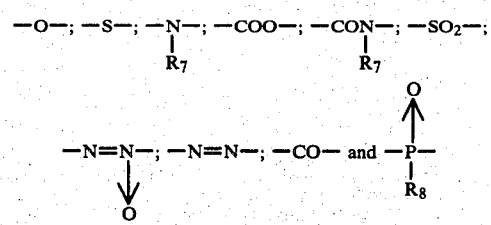

(wherein $R_7$ and $R_8$ independently represent an alkyl radical having from 1 to 4 carbon atoms such as methyl, ethyl, n-propyl and n-butyl; a cyclohexyl radical or a phenyl radical, and $R_7$ can also represent a hydrogen atom), and/or by an alkylene or alkylidene group having from 1 to 4 carbon atoms, such as methylene, ethylene and isopropylidene.

Amongst the radicals which have just been mentioned, G more particularly represents the following divalent and trivalent radicals:

(a) a straight or branched alkylene, alkylidene, alkenylene or alkenylidene radical having from 1 to 12 carbon atoms or a cycloalkylene or cycloalkenylene radical having from 5 to 8 nuclear carbon atoms.

By way of illustration, the following radicals may be mentioned: methylene; ethylene; propylene; butylene; hexamethylene; cyclohexylene.

(b) An arylene radical such as m-phenylene; p-phenylene; toluylene, such as 5-methyl-1,3-phenylene and 2-methyl-1,4-phenylene; a xylylene radical such as 1,2-dimethyl-3,6-phenylene; naphthylene; anthracenylene.

(c) A heterocyclic, saturated or unsaturated or aromatic radical containing one or more hetero-atoms O, N and S and 4 to 6 atoms in the ring, optionally substituted by one or two methyl groups.

The following radicals may be mentioned by way of illustration:

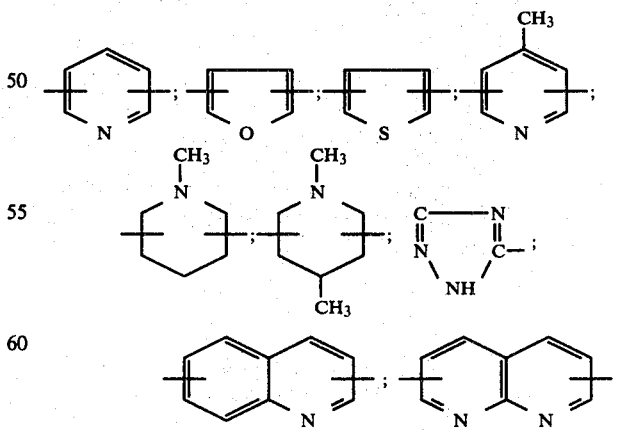

(d) A divalent radical consisting of a chain of 2 to 4 groups chosen from amongst those defined under (a) and/or (b) and/or (c), linked to one another by a valency bond and/or by at least one of the groups

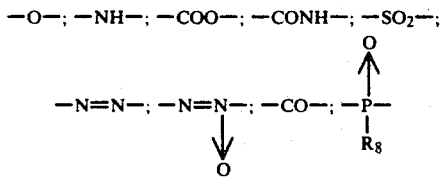

and/or by an alkylene and/or alkylidene group having from 1 to 4 carbon atoms, such as those already mentioned.

As examples of such groups, the following radicals may be mentioned:

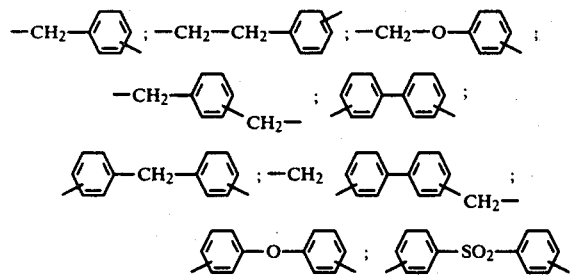

Preferably, G represents an alkylene or alkylidene radical having from 1 to 6 carbon atoms; a cyclohexylene radical; a m- or p-phenylene radical; toluylene; xylylene; a radical formed by two phenylene groups linked to one another by a valency bond or by an alkylene or alkylidene group having from 1 to 4 carbon atoms (such as methylene; ethylene; propylene; isopropylidene); an oxygen atom; one of the following groups:

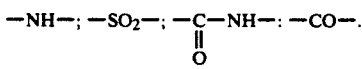

(e) A trivalent radical such as:
a benzenetriyl radical such as 1,2,4-benzenetriyl,
a naphthalenetriyl radical such as 2,3,6-naphthalenetriyl, and
a radical of the formula

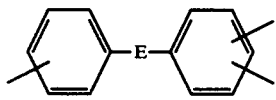

in which E represents a valency bond or an alkylene or alkylidene group having from 1 to 4 carbon atoms, such as those already mentioned, or one of the following groups:

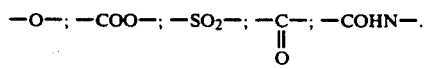

Amongst the trivalent groups G more preferentially represents the following groups:

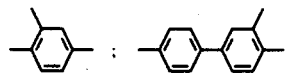

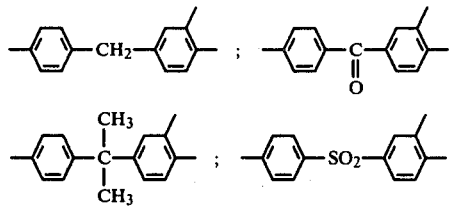

Preferably in the compounds of the formula (I) the various symbols have the following meanings:

n is an integer equal to 1 or 2,

R is a linear alkenyl group having from 2 to 6 carbon atoms, and especially a vinyl or allyl radical, $R_1$ is an alkyl group having from 1 to 5 carbon atoms, optionally substituted by 1 to 4 atoms of chlorine and/or fluorine, or a phenyl group, $R_2$ is a methylene or ethylene group and X is one of the following groups:

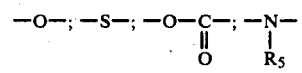

(wherein $R_5$ represents a hydrogen atom or a methyl radical).

G: a straight or branched alkylene radical having from 1 to 6 carbon atoms; a cyclohexylene radical; a phenylene, p-tolylene or xylylene radical; benzylene; a divalent radical consisting of two phenylene nuclei linked to one another by a valency bond or by one of the following groups: a methylene or isopropylidene group or —O—, —NH—, —SO$_2$—, —CO— or —CO—NH—; a trivalent radical such as the benzenetriyl radical or one of the following radicals:

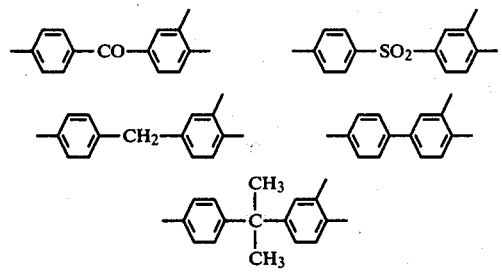

The following compounds of the formula (I) may be mentioned by way of illustration: 1-nitro-4-(vinyldimethylsilylmethoxy)-benzene, 1-nitro-(2-vinyldimethylsilyl-ethoxy)-benzene, 1-nitro-(3-vinyldimethylsilylpropoxy)-benzene, 1-methoxycarbonyl-4-(vinyldimethylsilylmethoxy)-benzene, 1-ethoxycarbonyl-4-(vinyldimethylsilylmethoxy)-benzene, 1-carboxy-4-(vinyldimethylsilylmethoxy)-benzene, 1-amino-4-(vinyldimethylsilylmethoxy)-benzene, 1-amino-4-(vinyldimethylsilylmethoxycarbonyl)-benzene, 1-ethoxycarbonyl-4-(allyldimethylsilylmethoxy)-benzene, 1-nitro-4-(methyldivinylsilylmethoxy)-benzene, 1-methoxycarbonyl-4-(2-methyldivinylsilylethoxy)-benzene, 1-nitro-4-(vinyldiphenylsilylmethoxy)-benzene, 1-nitro-[vinylbis(3,4-dichlorophenyl)silylmethoxy]-benzene, 1-nitro-4-(allyldimethylsilylmethoxy)-benzene, 1-nitro-4-[(but-1-enyl)dimethylsilylmethoxy]-benzene, 1-nitro-4-[(dimethylvinylsiloxy)dimethylsilylmethoxy]-benzene, 1-nitro-4-[(1,2,2-trichlorovinyl)dimethylsilylmethoxy]-benzene, 1-nitro-4-(methylphenylvinylsilylmethoxy)-benzene, 1-nitro-4-(methyl-γ-cyanopropylvinylsilylmethoxy)-benzene, 1,2-dinitro-4-(vinyldimethylsilylmethoxy)-benzene, the ethyl ester of 4-(vinyldimethylsilylmethoxy)-butanoic acid, the ethyl ester of 2-(vinyldimethylsilylmethoxy)-acetic acid, 3-ethoxycarbonyl-4-(vinyldimethylsilylmethoxy)-pyridine, 1-ethoxycarbonyl-4-(vinyldimethylsilylmethylthio)-benzene, 1-nitro-4-(vinyldimethylsilylmethylthio)-benzene, 1-nitro-4-(allyldimethylsilylmethylthio)-benzene, 1-nitro-4-(vinyldimethylsilylmethoxycarbonyl)-benzene, 1-ethoxycarbonyl-4-(vinyldimethylsilylethoxycarbonyl)-benzene, 1-ethoxycarbonyl-4-(allyldimethylsilylmethoxycarbonyl)-benzene, 1-ethoxycarbonyl-4-(vinyldimethylsilylmethoxycarbonyl)-benzene, 1-ethoxycarbonyl-4-(vinyldimethylsilylmethylthiocarbonyl)-benzene, 1-ethoxycarbonyl-4-(vinyldimethylsilylmethylthio-thiocarbonyl)-benzene, the ethyl ester of 2-(vinyldimethylsilylmethyl)-thioglycollic acid, N-p-nitrophenyl,N-vinyldimethylsilylmethylmethylamine, N-p-ethoxycarbonylphenyl,N-vinyldimethylsilylmethyl-methylamine, 1-chlorocarbonyl-4-(vinyldimethylsilylmethoxy)-benzene, 1-amino-4-(vinyldimethylsilylmethoxycarbonyl)-benzene, 1-carboxy-4-(vinyldimethylsilylmethoxycarbonyl)-benzene, 1-cyano-4-(vinyldimethylsilylmethoxycarbonyl)-benzene, 1-ethoxy-4-(vinyldimethylsilylmethoxycarbonyl)-benzene, 1-isocyanato-4-(vinyldimethylsilylmethoxy)-benzene, 1-aminomethyl-4-(vinyldimethylsilylmethoxy)-benzene, 1,2-bis-methoxycarbonyl-4-(vinyldimethylsilylmethoxy)-benzene, 1,2-bis-methoxycarbonyl-4-(vinyldimethylsilylmethoxy-carbonyl)-benzene, 4-vinyldimethylsilylmethoxy-4'-ethoxy-diphenylmethane, 4-vinyldimethylsilylmethoxy-4'-nitro-diphenylmethane, 4-vinyldimethylsilylmethoxy-4'-methoxycarbonyl-diphenylmethane, 4-vinyldimethylsilylmethoxy-4'-methoxycarbonyl-diphenylsulphone, 4-vinyldimethylsilylmethoxy-4'-methoxycarbonyl -diphenyl ether, 4-vinyldimethylsilylmethoxycarbonyl-4'-methoxycarbonyl-diphenylmethane, N-methyl-4-(vinyldimethylsilylmethoxy)-phthalimide, 1-methoxycarbonyl-4-(divinylmethylsilylmethoxy)-benzene, 1-chlorocarbonyl-4-(divinylmethylsilylmethoxy)-benzene and 4-(divinylmethylsilylmethoxy)-benzoic acid.

The organo-silicon compounds (I) can be obtained according to a process which consists of reacting:

(a) an organo-silicon compound (II) containing a chloroalkyl group and having the formula:

$$(R)_n-\underset{\underset{(R_1)_{3-n}}{|}}{Si}-R_2-Cl \quad (II)$$

with (b) a compound of the formula (III)

$$Z-X+G(Y_1)_m] \quad (III)$$

in which Z represents a hydrogen atom, an alkali metal or an ammonium group of the formula $$[(R_9)_3NH]-$$

where $R_9$ represents an alkyl group having from 1 to 4 carbon atoms. The symbol $Y_1$ represents a functional group such as those defined above for Y, but $Y_1$ is a functional group which is inert during the reaction.

If X represents an oxygen atom, a sulphur atom or a carboxyl or thiocarboxyl group, Z is preferably a sodium, potassium or lithium atom, or an ammonium group $[(R_9)_3NH]-$. For convenience, the alkali metal salts and the tertiary amine salts of the acids or of the phenols have been represented by a formula which uses covalent bonds. Obviously, these compounds can be employed in the ionic form.

If X represents a

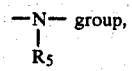 group,

Z is preferably H.

As has just been seen, the process according to the invention consists of reacting, by bringing into contact, an organo-silicon compound having a chloroalkyl group with a compound such as a phenate, carboxylate, thiocarboxylate, thiolate or amine. The amine compound can optionally be used in the form of its hydrochloride.

As has been indicated, the functional group $Y_1$ is a group which is inert during the condensation reaction. This group $Y_1$ must not be able to react with the chloroalkyl group of the silicon derivative or with the Z—X— group. Equally, this group $Y_1$ must not be able to react with another group Y. The nature of the radicals $Y_1$ can easily be deduced by those skilled in the art from the nature of the compounds (II) and (III). The compounds (I) obtained directly from the organo-silicon compounds with chloroalkyl groups and the compounds $Z-X+G(Y_1)_m]$ will hereafter be referred to as compounds (Ia).

By way of indication, if Z—X— represent a group containing an alkali metal atom or a quaternary ammonium group, $Y_1$ can be one of the following functional groups:

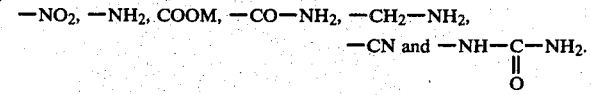

If Z—X— represents an amino group, the group $Y_1$ can be

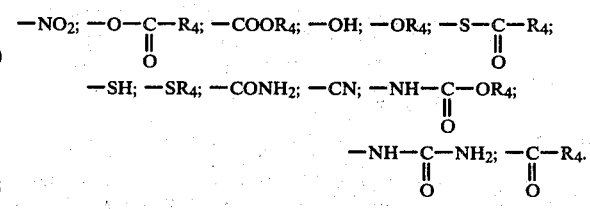

Starting from the compounds (Ia) defined above, it is possible to obtain, in accordance with the conventional methods of organic chemistry, other compounds (I), referred to as (Ib), which contain functional groups Y different from the $Y_1$ groups and which are by nature capable of reacting with one of the following groups: chloroalkyl, Z—X— or a $Y_1$ group. These compounds (Ib) contain, for example, Y groups such as —COCl; —NCO; —CHO. For example, the nitro derivatives can be converted to their corresponding amine or isocyanato derivatives. It is also possible to obtain the corresponding acids and acid chlorides.

The organo-silicon compounds (II) can be obtained in accordance with the general methods for obtaining organo-silicon derivatives having chloroalkyl groups. For this purpose, it is usual to prepare chloroalkylchlorosilanes, which are converted by a Grignard reaction to the corresponding ethylenic organo-silicon compounds. These methods are described, for example, in the treatise by Eaborn: Organosilicon Compounds, p. 379–381 (1960).

Purely by way of illustration, the following compounds may be mentioned amongst the organo-silicon compounds (II): vinyldimethylchloromethylsilane, allyldimethylchloromethylsilane, methyldivinylchloromethylsilane, vinyldiphenylchloromethylsilane, allyldiphenylchloromethylsilane, vinyldimethylchloroethylsilane, vinyldimethyl-n-chloropropylsilane, but-1-enyl-dimethylchloromethylsilane, 1,2,2-trichlorovinyldimethylchloromethylsilane, vinylmethylphenylchloromethylsilane, γ-cyanopropyl-vinylmethylchloromethylsilane, and 1,1,3,3-tetramethyl-3-vinyl-1-chloromethyl-disiloxane.

The compounds of the formula (III) can be amine compounds such as p-ethoxycarbonylphenylmethylamine, p-nitrophenylmethylamine and N-methyl-4-amino-4′-nitrodiphenylmethane, or alkali metal salts or tertiary amine salts of carboxylic or thiocarboxylic acids such as p-methoxybenzoic acid, the monoethyl ester of terephthalic acid, the monomethyl ester of diphenylmethane-4,4′-dicarboxylic acid, p- or m-nitrobenzoic acid, 3,4-dinitrobenzoic acid and p-nitrothiobenzoic acid.

These compounds (III) can also be alkali metal alcoholates or thiolates such as the salts of the following compounds: methyl p-hydroxybenzoate; p-hydroxynitrobenzene; 4-hydroxy-4′-nitro-diphenylmethane; 4-hydroxy-4′-ethoxydiphenyl ether; ethyl 4-mercaptobenzoate; 4-mercapto-nitrobenzene; 4-mercaptoethoxybenzene; the ethyl ester of thioglycollic acid; the methyl ester of 4-hydroxy-butanoic acid.

The condensation reactions of the organo-silicon compound (II) and of the compound (III) can be carried out in accordance with the general processes described in the literature relating to the nucleophilic substitution reactions which employ an organo-silicon compound with a chloroalkyl group; [see, e.g, Eaborn; Organosilicon Compounds, p.393; 411; 412; 413 (1960) and U.S. Pat. Nos. 2,783,262; 2,783,263 and 2,833,802].

As a general rule, the condensation reaction is carried out at a temperature of between 0° and 150° and preferably between 20° and 100° C., by gradually introducing one of the reactants into the reaction medium containing the other reactant. In general, the reaction is carried out in a solvent medium consisting of alcohols, such as methanol or ethanol, polar aprotic solvents such as N-methylpyrrolidone, dimethylformamide, dimethylacetamide and hexamethylphosphotriamide, or organic ethers, such as the methyl ether of diglycol. Once the reaction has been completed, the compounds (I) are isolated from the reaction medium by any known means such as, for example, distillation or fractional crystallisation.

The compounds according to the invention are very valuable synthesis intermediates in organo-silicon chemistry by virtue of the simultaneous presence in their molecule of an ethylenic group and of at least one other functional group. Thus it is possible, for example, to add onto the ethylenic double bond a hydrogenosilane which itself carries a functional group. This produces molecules which simultaneously contain two silicon atoms and two functional groups such as carboxyl, amine, hydroxyl or mercapto groups and the like, and these molecules open the way to a variety of polymers such as polyesters, polyamides, polyurethanes, polyimides and the like.

The compounds of the formula (I) are very particularly suitable for the synthesis of unsaturated disilanes with carbo-functional units, which form a second subject of the present invention.

B. More particularly, a second subject of the invention resides in the polyethylenic silicon compounds of the general formula:

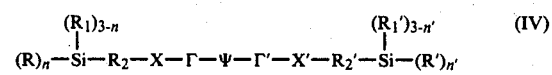

(IV)

in which R and R′, $R_1$ and $R'_1$, n and n′, $R_2$ and $R'_2$, and X and X′, which may be identical or different, have the general and specific meanings already given for the compounds (I), and Γ and Γ′ are identical or different organic radicals having from 1 to 30 carbon atoms, chosen from the groups consisting of:

(a) divalent radicals —G— and —G′— and
(b) trivalent radicals

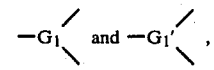

G, G′, $G_1$ and $G'_1$ having the meanings given to G for formula (I) and

Ψ is an organic radical chosen from the group consisting of:

(a) —β—C(=O)—β′—     (V)

(b) —T—R″—T′—     (VI)

(c) (VII)

(d) (VIII)

In the formulae V to VIII: β and β′ independently represent an oxygen or nitrogen atom, R″ represents a valency bond or a divalent organic radical, R‴ represents a trivalent organic radical, R⁗ represents a tetravalent organic radical and T and T′ represent identical or different functional groups chosen from the group consisting of:

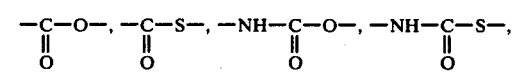

-continued

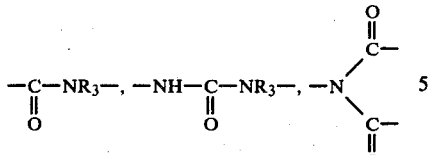

In the formulae, $R_3$ has the meaning already given.

More precisely, the various preceding symbols can assume the following meanings:

I-Radicals R and R'; $R_1$ and $R'_1$; $R_2$ and $R'_2$; X and X'; G and G'; $G_1$ and $G'_1$; n and n':

They can assume all the specific meanings mentioned for R, $R_1$, $R_2$, X, G and n for the formula (I).

II-RADICAL R''

It symbolises more particularly:

(1) A saturated or unsaturated, aliphatic, straight or branched, or cycloaliphatic, hydrocarbon radical optionally substituted by one or more chlorine atoms, or a monocyclic or polycyclic arylene radical of which the rings form, with one another, ortho-condensed or ortho- and peri-condensed systems.

These aromatic radicals can be substituted by halogen atoms; alkyl radicals having from 1 to 4 carbon atoms, such as methyl and ethyl radicals; alkenyl radicals having from 2 to 4 carbon atoms, preferably α- or β-ethylenic radicals; or by one or more functional groups such as cyano, ether, urethane, amide, ester (especially methylcarboxy and methoxycarbonyl), nitro, amino, hydroxyl and hydroxycarbonyl.

(2) A saturated, unsaturated or aromatic, monocyclic or polycyclic, heterocyclic radical containing at least one of the hetero-atoms O, N and S, and optionally substituted by methyl radicals.

(3) A divalent radical consisting of a chain of groups as defined in paragraphs 1 and/or 2 and linked to one another by:
a valency bond,
and/or at least one of the following groups:

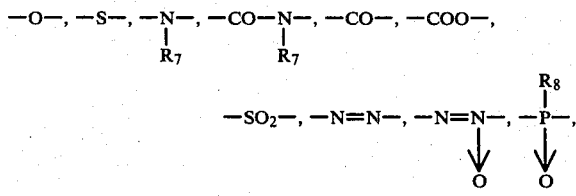

in which formulae $R_7$ and $R_8$ have the meaning already indicated,
or an organic radical containing silicon such as

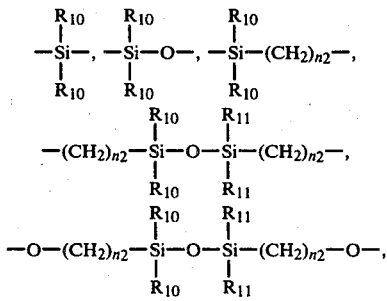

-continued

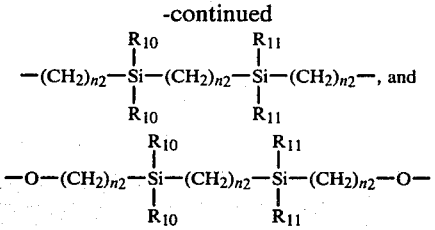

In these formulae, $n_2$ represents an integer from 1 to 3, and $R_{10}$ and $R_{11}$, which may be identical or different, represent an alkyl group having from 1 to 6 carbon atoms, an alkenyl radical having from 2 to 4 carbon atoms, preferably an α- or β-ethylenic radical, a phenyl group or a hydrolysable group chosen from the following:

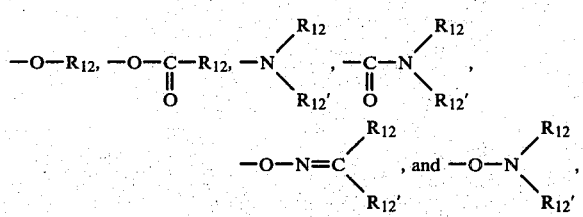

wherein $R_{12}$ and $R_{12}'$, which may be identical or different, represent alkyl groups having from 1 to 3 carbon atoms.

Amongst the radicals which have just been mentioned, R'' represents more particularly:

(a) a straight chain or branched alkylene, alkylidene, alkenylene or alkenylidene radical having at most 12 carbon atoms, or a cycloalkylene or cycloalkenylene radical having 5 to 8 carbon atoms in the ring.

By way of illustration, there may be mentioned the methylene, ethylene, ethylidene, cyclohexylene and butylene radicals.

(b) A phenylene, tolylene, xylylene and naphthylene radical optionally substituted by one or more chlorine atoms, nitrile, amide or ester (especially methylcarbonyloxy and methoxycarbonyl) groups, or alkyloxy radicals having from 1 to 4 carbon atoms, such as the methoxy radical.

(c) A saturated, unsaturated or aromatic monocyclic heterocyclic radical containing as the hetero-atom one or more oxygen, nitrogen or sulphur atoms, and containing 4 to 6 (total) atoms in the ring; the heterocyclic radicals can be substituted by one or two methyl groups.

The following radicals may be mentioned by way of illustration:

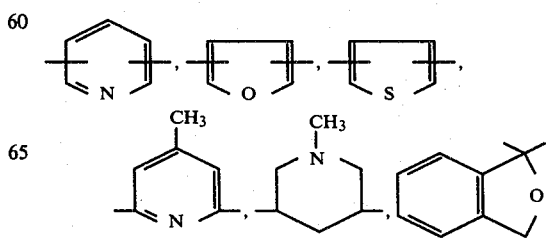

-continued

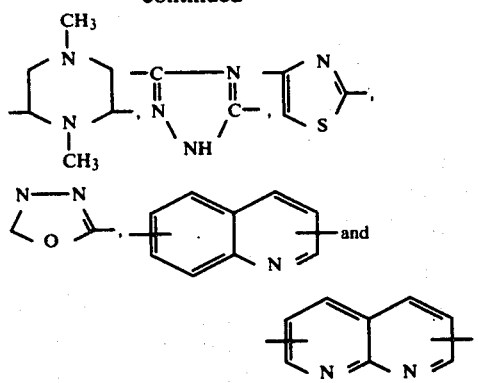

(d) A divalent radical consisting of a chain of two to four groups as defined in paragraphs a and/or b and/or c and linked to one another by a valency bond and/or by at least one of the following groups:

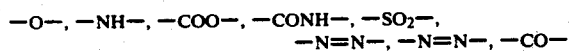

and/or by an alkylene or alkylidene group having from 1 to 4 carbon atoms, or by an organic radical containing silicon, such as:

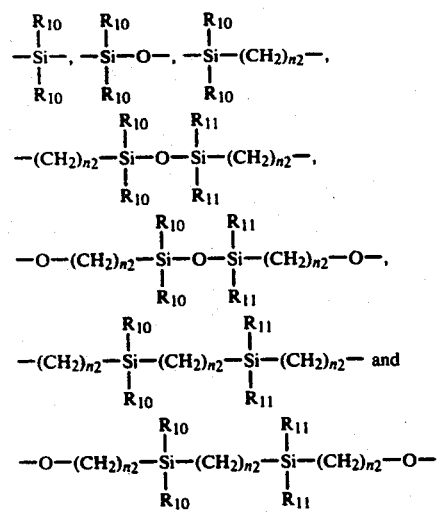

(wherein $n_2$ represents an integer from 1 to 3, and $R_{10}$ and $R_{11}$ denote a methyl or phenyl radical).

By way of illustration, the radicals of the following formulae may be mentioned:

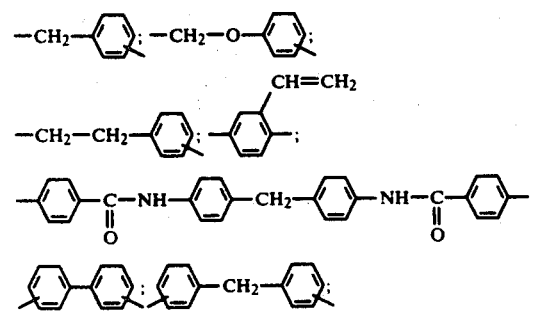

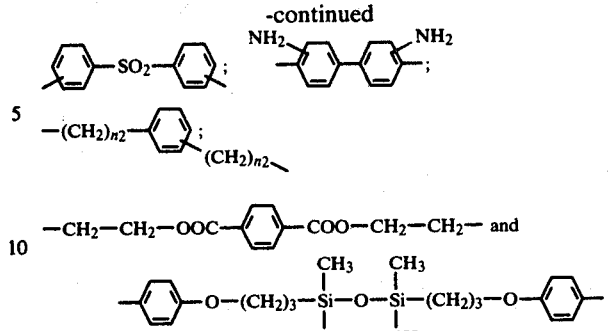

Preferably, R" represents:
an alkylene radical having from 1 to 8 carbon atoms, a cyclohexylene radical, a phenylene, tolylene or xylylene radical, or a pyridylene radical, or
a divalent radical containing 2 to 4 phenylene groups linked to one another by a valency bond, by an oxygen atom, by one of the groups:

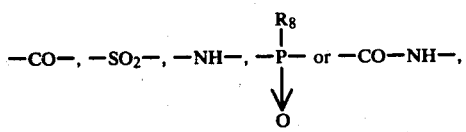

or by an alkylene or alkylidene group having from 1 to 4 carbon atoms, or by an organic radical containing silicon, such as:

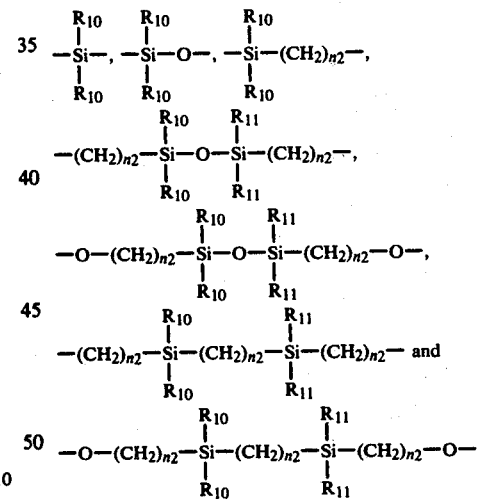

(wherein $n_2$ represents an integer from 1 to 3 and $R_{10}$ and $R_{11}$ denote a methyl or phenyl radical), or
a divalent radical containing 2 alkylene groups having from 1 to 4 carbon atoms linked to a phenylene group by a valency bond, by an oxygen atom or by one of the groups:

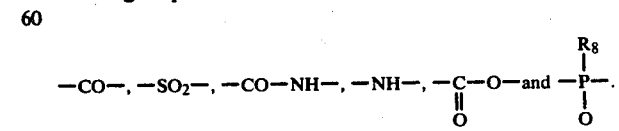

III-RADICALS R''' and R''''

R''' and R'''' are multivalent radicals which can be:

(1) A linear or branched saturated aliphatic hydrocarbon radical having from 2 to 20 carbon atoms.

(2) A saturated or unsaturated alicyclic hydrocarbon radical containing from 5 to 6 carbon atoms in the ring.

(3) A saturated or unsaturated heterocyclic radical containing at least one of the atoms O, N and S and from 4 to 6 atoms in the ring.

(4) A monocyclic or polycyclic aromatic hydrocarbon radical in which the rings are fused or are linked to one another by a valency bond or by an alkylene or alkylidene radical having from 1 to 4 carbon atoms or by one of the following groups:

—O—, —S—, —NH—, —COO—, —CO—, —CO—NL—,
—SO$_2$—, —N=N—, —N=N—, —CO—NL—Δ—,
$$\downarrow$$
$$O$$

$$-CO-O-\Delta-O-CO- \text{ and } -\overset{R_8}{\underset{\downarrow}{P}}- \text{ in which } \Delta$$
$$O$$

in which Δ represents a linear or branched alkylene radical having fewer than 13 carbon atoms, a cycloalkylene radical with 5 or 6 carbon atoms in the ring or a monocyclic or polycyclic arylene radical, and L represents a hydrogen atom, an alkyl radical having from 1 to 4 carbon atoms or a phenyl radical. Furthermore, these aromatic radicals can be substituted by methyl groups and/or chlorine atoms.

More particularly, R''' and R'''' represent:

(a) a linear or branched saturated aliphatic hydrocarbon radical having from 2 to 10 carbon atoms.

By way of illustration, the following radicals may be mentioned:

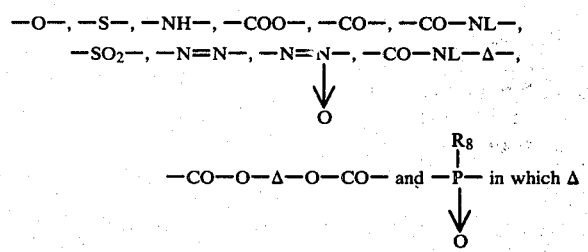

(b) a saturated or unsaturated alicyclic hydrocarbon radical having from 5 or 6 carbon atoms in the ring. These radicals are, for example, the following:

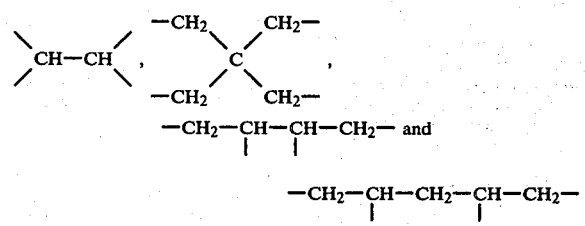

(c) a saturated or unsaturated heterocyclic radical containing 5 or 6 atoms in the ring and containing at least one of the atoms O, N and S.

By way of illustration, the heterocyclic radicals of the following formulae may be mentioned:

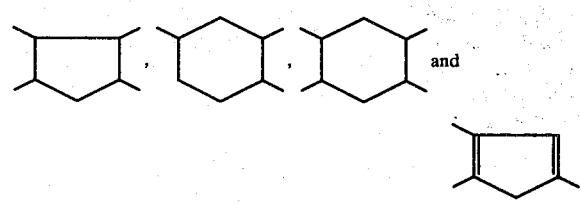

(d) a monocyclic or polycyclic hydrocarbon radical in which the rings are fused or linked to one another by a valency bond or by an alkylene or alkylidene group having from 1 to 4 carbon atoms, such as the methylene, ethylene and isopropylidene radicals, by an oxygen atom or by one of the following groups:

$$-CO-, -COO-, -SO_2-, -CO-NH- \text{ and } -\overset{R_8}{\underset{\downarrow}{P}}-.$$
$$O$$

By way of illustration, R''' and R'''' can represent one of the radicals

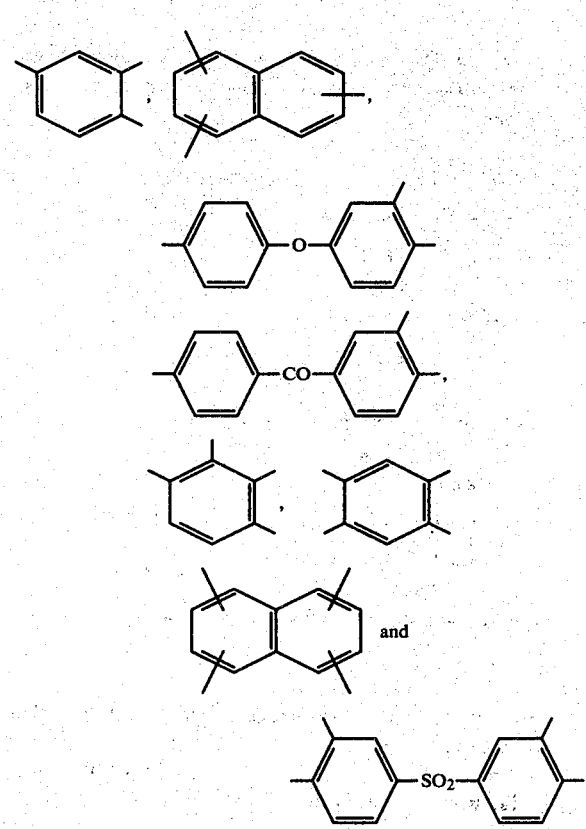

Preferably, R''' and R'''' are trivalent or tetravalent radicals containing 1 or 2 benzene nuclei linked to one another by a valency bond, an oxygen atom, a methylene or isopropylidene radical or one of the groups:

$$-CO-, -SO_2- \text{ and } -\overset{R_8}{\underset{\downarrow}{P}}-.$$
$$O$$

IX-GROUPS T and T'

T and T' preferably represent one of the following groups:

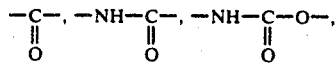

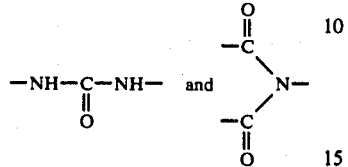

Amongst these compounds of the formula (IV), the compounds more particularly claimed are those for which the various radicals of the said formula have the following meanings:

n and n': an integer equal to 1.

R and R': a linear alkenyl group having from 2 to 6 carbon atoms and especially a vinyl or allyl group.

$R_1$ and $R_1'$: an alkyl radical having from 1 to 5 carbon atoms, optionally substituted by 1 to 4 atoms of chlorine and/or fluorine, or a phenyl radical.

$R_2$ and $R_2'$: a methylene or ethylene group.

X and X': one of the following groups:

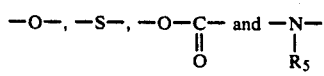

wherein $R_5$ represents a hydrogen atom or a methyl or ethyl radical.

$\beta$ and $\beta'$: an oxygen atom.

G and G': an alkylene or alkylidene radical having from 1 to 6 carbon atoms, a cyclohexylene radical, a phenylene, tolylene or xylylene radical, a radical formed by two phenylene groups linked to one another by a valency bond, a methylene or isopropylidene group, an oxygen atom or one of the groups —NH—, —SO$_2$—, —CO— and —CO—NH—.

$G_1$ and $G_1'$: a 1,2,4-benzenetriyl radical or a trivalent radical containing two benzene nuclei linked to one another by a valency bond or a carbonyl, sulphone, methylene or isopropylidene group.

R'': an alkylene radical having from 1 to 8 carbon atoms, a cyclohexylene radical, a phenylene, tolylene or xylylene radical or a pyridylene radical, a divalent radical containing from 2 to 4 phenylene groups linked to one another by a valency bond, by an oxygen atom or by one of the following groups:

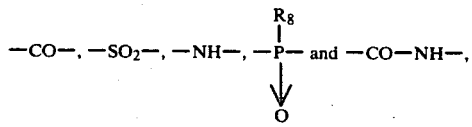

or by an alkylene or alkylidene group having from 1 to 4 carbon atoms, or by an organic radical containing silicon, such as:

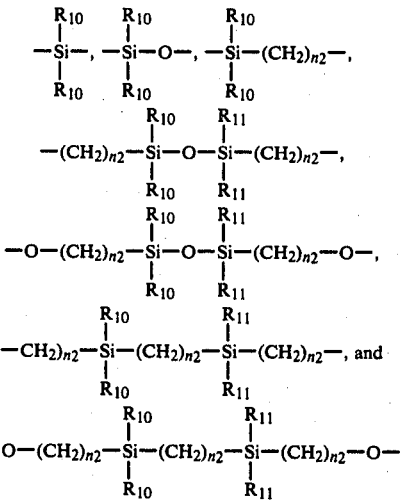

(wherein n represents an integer from 1 to 3 and $R_{10}$ and $R_{11}$ denote a methyl or phenyl radical), or a divalent radical containing 2 alkylene groups having from 1 to 4 carbon atoms linked to a phenylene group by a valency bond, by an oxygen atom or by one of the groups:

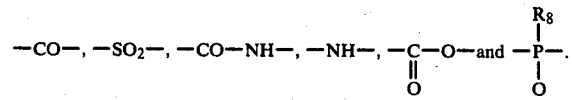

R''' and R'''': trivalent or tetravalent radicals containing 1 or 2 benzene nuclei linked to one another by a valency bond, by an oxygen atom, by a methylene or isopropylidene radical or by one of the groups

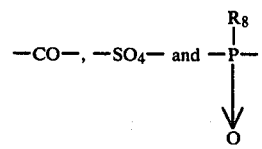

(wherein $R_8$ has the meaning given above).

$R_3$: denotes a hydrogen atom or a methyl group.

T and T': one of the following groups:

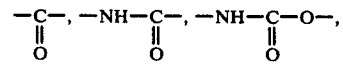

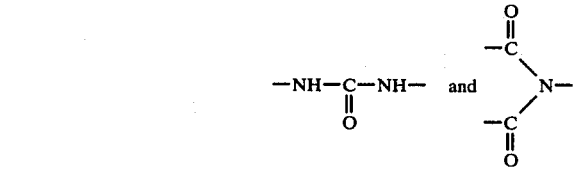

By way of illustration, the following compounds of the formula (IV) may be mentioned:

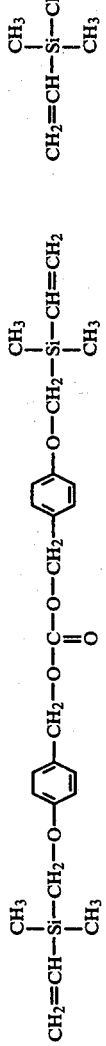
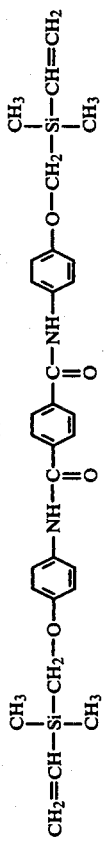
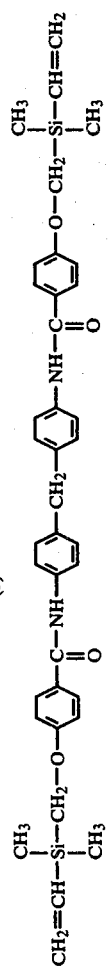
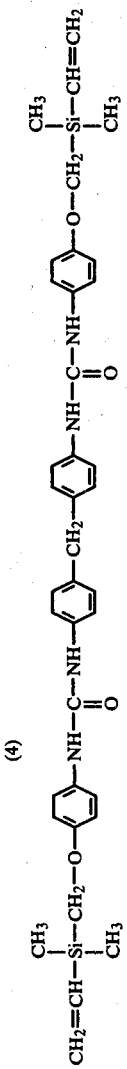
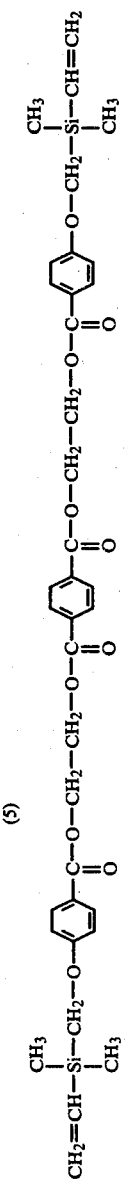
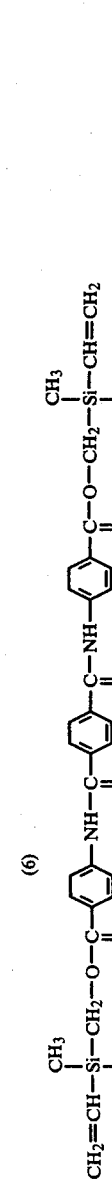
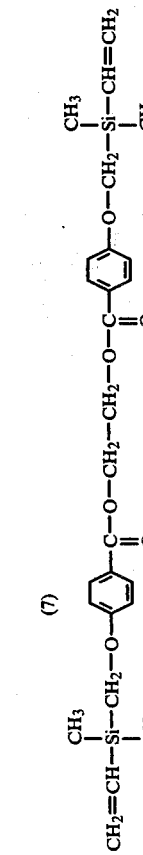

-continued
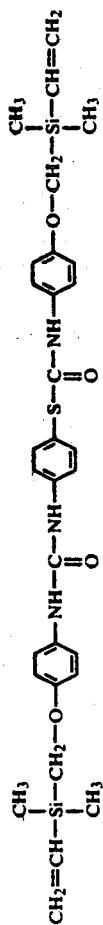
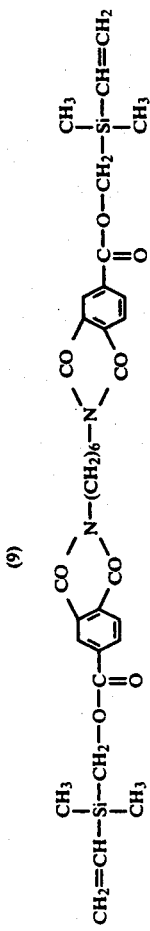
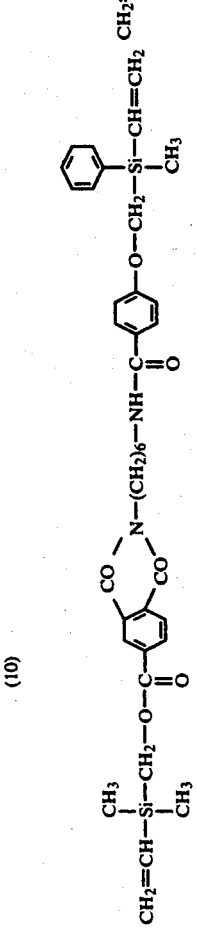
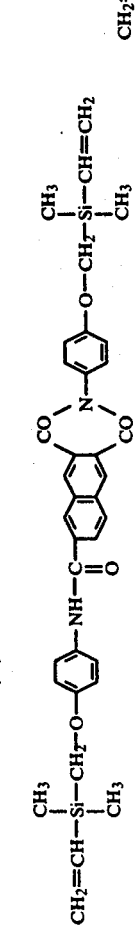
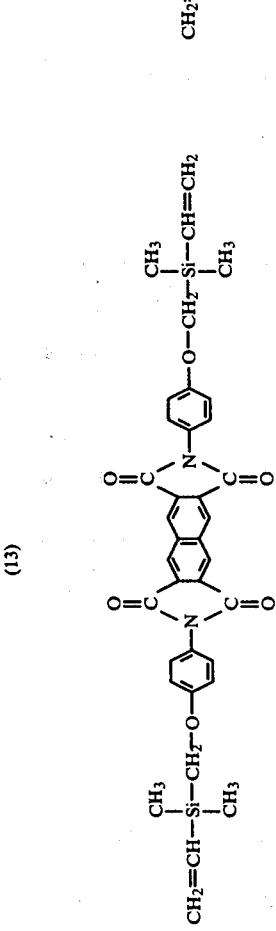
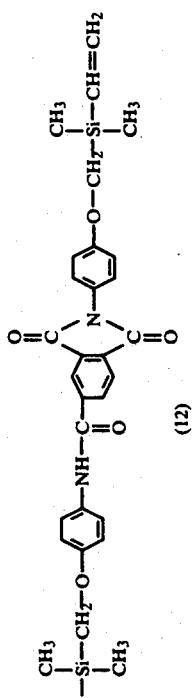
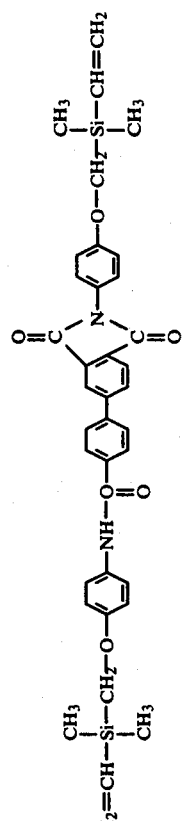
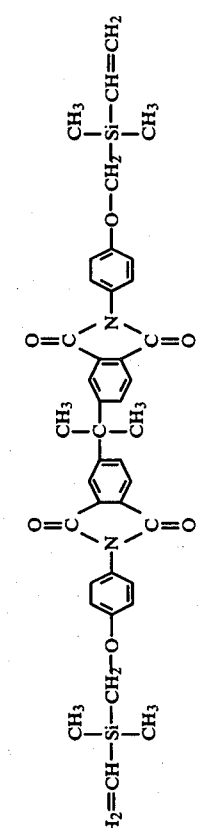

-continued
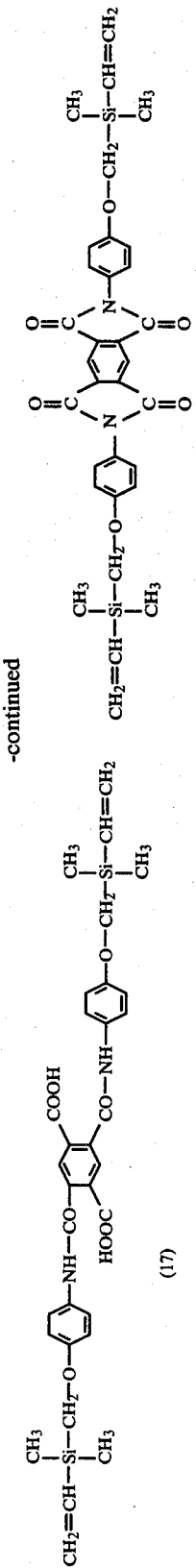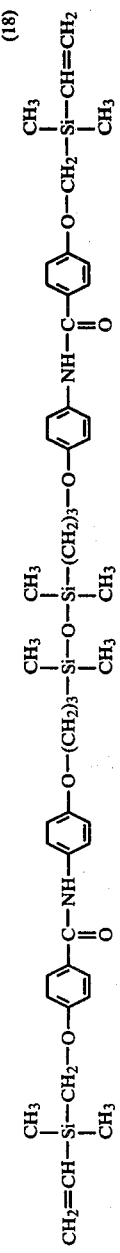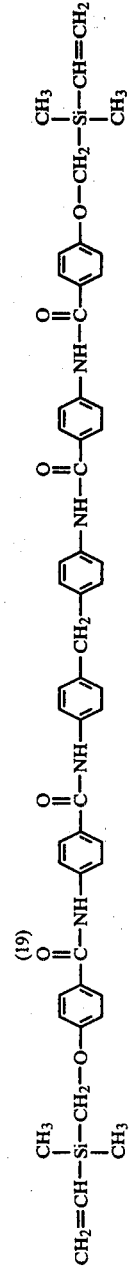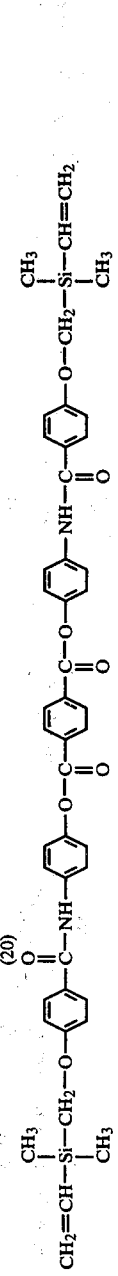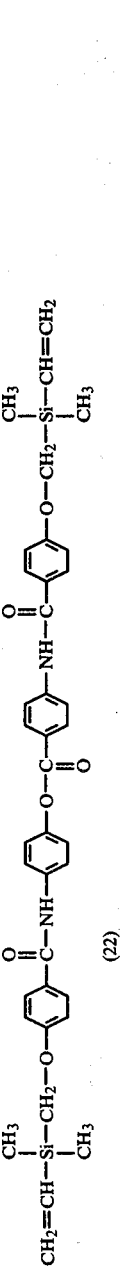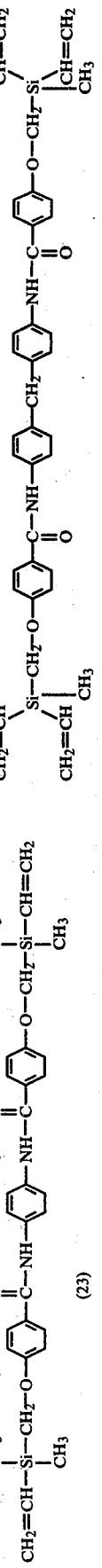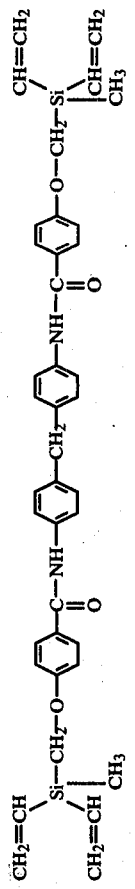

Obviously, compounds analogous to the compounds (1) to (24), obtained by replacing the vinyl group by an allyl group, could be mentioned.

The compounds of particular interest are those in which the numbers n and n' are identical and the radicals and groups R, $R_1$, $R_2$, $R_3$, X, G, $G_1$, $\beta$ and T are respectively identical to R', $R'_1$, $R'_2$, $R'_3$, X', G', $G_1'$, $\beta'$ and T'.

The compounds preferred are those of the formula (3), (4), (5), (6), (7), (17), (18), (19), (20), (21), (22), (23) and (24).

PREPARATION OF THE POLYETHYLENIC SILICON COMPOUNDS OF THE FORMULA (IV)

The compounds corresponding to the general formula (IV) can be obtained in accordance with a process which consists of reacting (1) an organo-silicon compound of the general formula (I) corresponding to the formula (A):

by itself, or together with an organo-silicon compound of the formula (A')

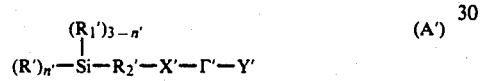

with (2) a compound hereafter referred to as the coupling agent, of the formula (B)

In the formulae (A) and (A'), n, n', R, R', $R_1$, $R'_1$, $R_2$, $R'_2$, X, X', T and T' have the meanings already given for the formulae (I) and (IV). Y and Y', which may be identical or different, represent one of the following functional groups, chosen from amongst those mentioned for Y in connection with the formula (I)

| | |
|---|---|
| —OH | (IX) |
| —SH | (X) |
| —N=C=O | (XI) |
| —C—Cl<br>‖<br>O | (XII) |
| COOH | (XIII) |
| —C—O—$R_4$<br>‖<br>O | (XIV) |
| —N—H<br>  |<br>  $R_3$ | (XV) |
| —C—O—C—<br>‖    ‖<br>O    O | (XVI) | wherein $R_3$ and $R_4$ have the meanings already given, and T and T' represent:

G and G' if Y and Y' represent the groups (IX) to (XV), and/or $G_1$ and $G_1'$ if Y and Y' represent the group (XVI).

In the formula (B), $\Xi$ represents a

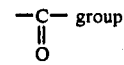

or one of the radicals R'', R''' and R'''', which have the meanings already given for the formulae (VI), (VII) and (VIII).

$T_1$ and $T_1'$, which may be identical or different, represent a chlorine atom or one of the groups defined for Y and Y'.

$\Xi$ represents a carbonyl group if $T_1$ and $T_1'$ represent a chlorine atom, and a radical R''' or R'''' if $T_1$ and $T_1'$ represent one or two anhydride groups.

More precisely, the compounds of the formula (B) correspond to the formulae

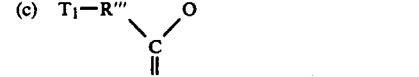

The coupling agent employed in the course of the synthesis of the compound (IV) can contain two identical or different groups $T_1$ and $T_1'$ which, naturally, should not be reactive towards one another under the conditions of carrying out the synthesis of the compounds of the formula (IV).

The compounds ($B_2$) and ($B_3$) are so chosen that the functional groups $T_1$ and/or $T_1'$ can react with the groups Y and/or Y' carried by the compounds (A) and/or (A').

Preferably, identical groups $T_1$ and $T_1'$ are chosen if a coupling agent corresponding to the formula ($B_2$) is employed.

If two compounds (A) and (A') which differ in respect of their group Y and Y' are reacted with the compound (B), they must be so chosen as to avoid any condensation between them under the conditions of the reaction.

The choice of the groups $T_1$, $T_1'$, Y and Y' can easily be decided by those skilled in the art on the basis of the nature of the silicon compounds and of the coupling agent.

By way of example, the synthesis of the compounds of the formula (IV) can be illustrated by the following reaction schemes:

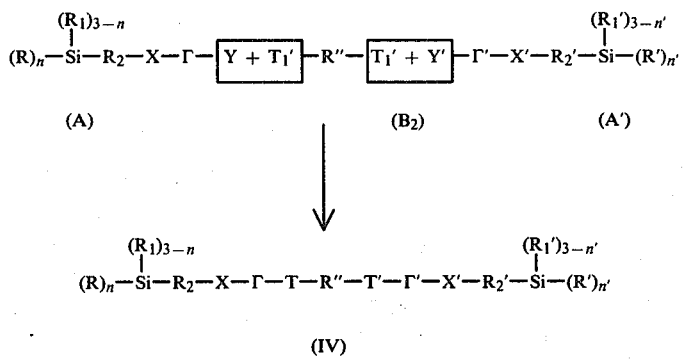

(IV)

Thus T and T' and β and β' previously defined result from the reaction between the groups Y, Y' and $T_1$, $T_1'$.

The amounts of reactants to be employed depend on the nature of the reactants brought together; they can be close to the stoichiometric amount or, without disadvantage they can differ therefrom.

In general, at least two mols of compound A (or 1 mol of each compound A and A') are reacted with one mol of compound B.

The condensation reactions of the organo-silicon compound or compounds and of the compound (B) are carried out in accordance with the general processes described in the literature and well known to those skilled in the art.

The organo-silicon compounds of the formula (IV) in which T and T' represent an amide group are obtained by condensation of a compound which carries an acid chloride group and a diamine compound. The reaction is, as a general rule, carried out at a temperature of from $-20°$ to 200° C. and preferably $-10°$ to 100° C. One of the reactants is gradually introduced into the reaction medium containing the other reactant. In general, the reaction is carried out in a medium which is an adequate solvent, consisting, for example, of acetone, dimethylacetamide, carbon tetrachloride or their mixtures, in the presence of the usual acceptors of hydrochloric acid. When the reaction has been completed, the compounds (IV) can be isolated from the reaction medium by any known means.

It is also possible to carry out this type of condensation at the interface of two immiscible solvents each containing one of the reactants and the acid acceptor [see N.O.V. SONNTAG—Chem. Rev. 52, 268–294 (1953), J. ZABICKY—The Chemistry of Amides (1970), p. 73 (Interscience Publishers)].

The organo-silicon compounds of the formula (IV) in which T and T' are ester groups can be prepared either directly by reaction of a compound having a free carboxylic acid group with a compound having a hydroxyl group, or by trans-esterification in the presence of the usual catalysts. In this latter case, the methyl ester of the acid compound is preferably used. It is also possible to obtain these compounds (IV) by reaction of the acid anhydrides or acid halides with the corresponding hydroxylic compounds, if appropriate in the presence of an acceptor for the hydracid [see KIRK-OTHMER, Encyclopaedia of Chemical Technology—2nd edition, 8, 313 to 339, and N.O.V. SONNTAG—Chem. Rev. 52, 312–321 (1953)].

The organo-silicon compounds (IV) with imide groups can be obtained in a manner which is in itself known by heating an acid anhydride with a compound having a primary amine group so as to give the corresponding imide directly. According to another method which is also known, it is possible to form, as an intermediate stage, the ammonium salt corresponding to the diacid and to the amine, in accordance with the usual methods, and then bring about the cyclisation by heating the salt, with elimination of water. It is also possible to form, as an intermediate, an acid amide which is subsequently dehydrated by heating.

In all cases, the temperature will be chosen in accordance with the reactants employed.

In general, this temperature is from 50° to 200° C. The formation of the imides can be carried out in organic solvents or diluents which are inert towards the reactants.

The organo-silicon compounds (IV) with urea or urethane groups are easily obtained from reactants containing, firstly, isocyanate groups, and, secondly, amine or hydroxyl groups, the reaction being carried out under the usual conditions for the reaction of isocyanates with compounds containing active hydrogen (see KIRK-OTHMER—Encyclopaedia of Chemical Technology, 2nd edition, 21, 63 to 74). In general, the reaction temperature, which can be varied in accordance with the compound, containing active hydrogen, which is employed, is from 0° to 100° C. and more particularly from 0° to 50° C. The condensation can be carried out in the presence of the usual catalysts (e.g. tertiary amines, metal halides, aluminium chloride, tin chloride, organo-silicon compounds and the like). The reaction can be carried out in bulk or preferably in suspension or in solution in a solvent which is inert towards the reactants, especially towards isocyanates. For example, aliphatic, cycloaliphatic or aromatic hydrocarbons or their chlorinated derivatives, or ethers, can be employed for this purpose.

REACTANTS EMPLOYED

I—Nature of the Coupling Agent

By way of illustration, the following compounds, which have two identical or different functional groups, may be mentioned amongst the coupling agents (B):

(1) corresponding to the formula $B_1$: phosgene.

(2) corresponding to the formula $B_2$:

(a) dicarboxylic acids and their derivatives (esters and acid chlorides):

As examples of dicarboxylic acids there may in particular be mentioned:

Aliphatic acids such as oxalic acid, malonic acid, succinic acid, glutaric acid, adipic acid, 2,4-dimethyladipic acid, pimelic acid, suberic acid, azelaic acid, sebacic acid, dodecanedioic acid, fumaric acid, maleic acid, methyliminodiacetic acid and 3-dimethylaminohexanedioic acid.

Cycloalkanedicarboxylic acids such as 1,4-cyclohexanedicarboxylic acid and 3-dimethylamino-1,2-cyclopentanedicarboxylic acid.

Aromatic diacids such as phthalic acid, isophthalic acid, terephthalic acid, phenylenediacetic acid, 1,5-naphthalenedicarboxylic acid, 1,6-naphthalenedicarboxylic acid, 4,4'-diphenyldicarboxylic acid, 3,3'-diphenyldicarboxylic acid, bis-(4-hydroxycarbonyl)-phenyl ether, bis-(3-hydroxycarbonyl)-phenyl ether, 4,4'-dihydroxycarbonyl-diphenylsulphone and 3,3'-dihydroxycarbonyl-diphenylsulphone.

Pyrimidine-dicarboxylic acids or imidazole-dicarboxylic acids.

It is also possible to use, as the coupling agent, the acid chlorides and the esters, preferably the methyl esters, obtained from these dicarboxylic acid compounds.

The diacids used preferentially are the following: oxalic acid, succinic acid, adipic acid, fumaric acid, isophthalic acid, terephthalic acid, 1,5-naphthalenedicarboxylic acid, 4,4'-diphenyldicarboxylic acid and 3,3'-diphenyldicarboxylic acid.

(b) The primary and secondary diamines:

Hexamethylenediamine, octamethylenediamine, decamethylenediamine, 2,5-dimethyl-heptamethylenediamine, bis-hexamethylenetriamine, diethylenetriamine, tetraethylenepentamine, bis-(4-aminocyclohexyl)-methane, 2,2-bis-(4-aminocyclohexyl)-propane, 1,4-diaminocyclohexane, m-phenylenediamine, p-phenylenediamine, m-xylenediamine, p-xylylenediamine, benzidine, bis-(4-aminophenyl)-methane, 2,2-bis-(4-aminophenyl)-propane, 4,4'-diaminodiphenyl ether, 4,4'-diaminodiphenyl sulphide, 4,4'-diaminodiphenyl-sulphone, 4,4'-diaminobenzophenone, 4,4'-diaminobenzanilide, 4,4'-diamino(phenyl benzoate), 3,3'-dicarboxybenzidine, 1,1-bis-(p-aminophenyl)-phthalane, 4,4'-N,N'-bis-(p-aminobenzoyl)-diamino-diphenylmethane, bis-p-(4-amino-phenoxycarbonyl)-benzene, bis-p-(4-aminophenoxy)-benzene, 1,5-diaminonaphthalene, 2,6-diaminopyridine, 6,6'-diamino-2,2'-dipyridyl, 2,5-bis-(m-aminophenyl)-1,3,4-oxadiazole, 2,5-bis-(p-aminophenyl)-1,3,4-oxadiazole, 2,5-bis-(m-aminophenyl)-thiazolo(4,5d)thiazole, 5,5'-di-(m-aminophenyl)-(2,2')-bis-(1,3,4-oxadiazolyl), 4,4-bis-(p-aminophenyl)-2,2'-dithiazole, m-bis-[4-(p-aminophenyl)-2-thiazolyl]-benzene, 2,2'-bis(m-aminophenyl)-(5,5')-dibenzimidazole, 3,5-diamino-1,2,4-triazole, 3,5-bis-(4-aminophenyl)-pyridine, bis-(4-aminophenyl)-methylphosphine oxide, bis-(4-aminophenyl)-phenylphosphine oxide, N,N'-bis-(4-aminophenyl)-methylamine, bis-(4-methylaminophenyl)-methane, bis-(4-methylaminophenyl)ether, 2,2-bis-(4-methylaminophenyl)-propane, bis-(3-methylaminophenyl)-sulphone, 1,3-bis-methylamino-benzene, bis-(4-methylaminocyclohexyl)-methane, N,N'-diethylhexamethylenediamine, 2,5-bis-methylamino-1,3,4-oxadiazole, 1,2-bis-( 3-methylaminopropoxy)-ethane, (4-methylaminophenyl) (4'-aminophenyl)-methane, 4-methylaminobenzene 4'-aminobenzene ether, 4-methylaminophenyl 4'-aminophenyl sulphone, 1-methylamino-4-amino-benzene, 2-methylamino-4-amino-toluene, 2-methylamino-5-amino-anisole, 3-methylamino-propylamine, 2-ethoxy-4-methylamino-aniline, 3'-methylamino-4-benzoylaminoaniline, 3-ethylaminoethoxy-propylamine, 3-ethylaminoethylmercapto-propylamine, 6-methylamino-hexylamine, (4-methylaminocyclohexyl)(4'-aminocyclohexyl)-methane, 2-p-methylaminophenyl-5-amino-1,3,4-oxadiazole, 2-m-methylaminophenyl-5-amino-benzoxazole, 1,3-bis-(3-p-aminophenoxypropyl)-tetramethyldisiloxane, 1,3-bis-(2-p-aminophenoxyethyl)-tetramethyldisiloxane, 1,2-bis-(2-p-aminophenoxyethyl-dimethylsilyl)-ethane and 4,4'-diamino-azobenzene.

The diamines used preferentially are the following:

Hexamethylenediamine, 2,2-bis-(4-aminocyclohexyl)-propane, m-phenylenediamine, p-phenylenediamine, m-xylenediamine, p-xylenediamine, bis-(4-aminophenyl)-methane, 4,4'-diaminodiphenyl ether, 4,4'-diaminobenzophenone, 4,4'-diamino(phenyl benzoate), 4,4'-N,N'-bis-(p-aminobenzoyl)-diaminodiphenylmethane, bis-p-(4-aminophenoxy)-benzene, 2,6-diaminopyridine, 2,5-bis-(p-aminophenyl)-1,3,4-oxadiazole, 4,4'-bis(p-aminophenyl)-2,2'-dithiazole, 3,5-diamino-1,2,4-triazole, 1,3-bis-(4-aminophenyl)-methylphosphine oxide, 1,3-bis-(2-p-aminophenoxyethyl)-tetramethyldisiloxane and 1,2-bis-(2-p-aminophenoxyethyl-dimethylsilyl)-ethane.

(c) Diisocyanates:

1,2-Diisocyanato-propane, 1,2-diisocyanato-butane, 1,3-diisocyanato-butane, 1,6-diisocyanato-hexane, 1,3-diisocyanato-benzene, 1,4-diisocyanato-benzene, 2,4-diisocyanato-toluene, 2,6-diisocyanato-toluene, 2,4-diisocyanato-xylene, 2,6-diisocyanato-xylene, 3,3'-diisocyanato-diphenyl, 4,4'-diisocyanato-diphenyl, 3,3'-diisocyanato-diphenylmethane, 4,4'-diisocyanato-diphenylmethane, 4,4'-diisocyanato-3,3'-dimethyl-diphenyl, 4,4'-diisocyanato-3,3'-dimethyl-diphenylmethane, 4,4'-diisocyanato-diphenylethane, 3,3'-diisocyanato-diphenyl ether, 4,4'-diisocyanato-diphenyl ether, 3,3'-diisocyanato-diphenylsulphone, 4,4'-diisocyanato-diphenylsulphone, 3,3'-diisocyanato-benzophenone, 4,4'-diisocyanato-benzophenone, 3,3'-diisocyanato-dicyclohexylmethane, 4,4'-diisocyanato-dicyclohexylethane, 1,5-diisocyanato-naphthalene, 4,4'-diisocyanato-3,3'-dichloro-diphenyl and 4,4'-diisocyanato-3,3'-dimethoxy-diphenyl.

The diisocyanates used preferentially are the following:

1,6-Diisocyanato-hexane, 2,4-diisocyanato-toluene, 2,6-diisocyanato-toluene, 2,4-diisocyanato-xylene, 4,4'-diisocyanato-diphenyl, 4,4'-diisocyanato-diphenylmethane, 4,4'-diisocyanato-diphenyl ether, 4,4'-diisocyanato-diphenylsulphone, 4,4'-diisocyanato-benzophenone, 4,4'-diisocyanato-dicyclohexylethane and 1,5-diisocyanato-naphthalene.

(d) Diols and diphenols:

Ethylene glycol, diethylene glycol, triethylene glycol, tetraethylene glycol, 1,3-propanediol, 1,2-propanediol, 1,4-butanediol, 1,3-butanediol, 1,5-pentanediol, 1,4-pentanediol, 1,3-pentanediol, 1,6-hexanediol, 1,7-heptanediol, 2,2-dimethyl-1,3-propanediol, 1,8-octanediol, 1,12-dodecanediol, 3,13-tetradecanediol, 2-ethyl-1,8-octanediol, 3-ethyl-1,10-decanediol, 3,6-diethyl-1,8-octanediol, 4,7-diethyl-2,9-decanediol, 2-butene-1,4-diol, 2-pentene-1,5-diol, 2-heptene-1,7-diol, 2-butine-1,4-diol, 1,4-cyclohexanediol, N-phenyldiethanolamine, 2,2'-sulphonyl-diethanol, 4,4'-sulphonyldibutanol, 3,3'-[sulphonyl-bis-(3-propyl-sulphonyl)]-dipropanol, 2,2'-(p-phenylenedioxy)-diethanol, 3,3'-(p-xylylenedioxy)-dipropanol, 4,4'-(p-phenylenedisulphonyl)-dibutanol, 6,6'-(p-xylylenedisulphonyl)-dihexanol, 2,2'-(4,4'-diphenylenedioxy)-diethanol, 1,4-bis-(β-hydroxyethyl)-cyclohexane, 1,4-bis-δ-hydroxybutyl)-cyclohexane, 4,4'-bis-(hydroxymethyl)-diphenyl, 2,6- bis-(hydroxymethyl)-naphthalene, 1,5-bis-(β-hydroxyethyl)-naphthalene, 1,4-bis-(β-hydroxyethyl)-benzene, 1,4-bis-(γ-hydroxypropyl)-benzene, 2-(β-hydroxyethyl)-benzyl alcohol, ethylene glycol terephthalate, hydroquinone, resorcinol, catechol, p-xylene glycol, 1,4-dihydroxynaphthalene, 1,5-dihydroxynaphthalene, 4,4'-dihydroxydiphenyl, bis-(4-hydroxyphenyl)-methane, bis-(4-hydroxyphenyl)-methylphenylmethane, bis-(4-hydroxyphenyl)-sulphone, 2,2-bis-(4-hydroxyphenyl)-propane and the bis-(4-hydroxyphenyl)-tolylmethanes.

The diols and diphenols used preferentially are the following:

Ethylene glycol, 1,3-propanediol, 1,4-butanediol, 1,5-pentanediol, 1,6-hexanediol, 1,7-heptanediol, 4,4'-(p-phenylenedisulphonyl)-dibutanol, 1,4-bis-(δ-hydroxybutyl)-cyclohexane, 1,4-bis-(β-hydroxyethyl)-benzene, hydroquinone, resorcinol, 1,5-dihydroxynaphthalene, 4,4'-dihydroxydiphenyl, bis-(4-hydroxyphenyl)-methane and bis-(4-hydroxyphenyl)-sulphone.

(d) Dithiols:

1,2-Ethanedithiol, 1,2-propanedithiol, 1,3-propanedithiol, 1,6-hexanedithiol, 2-butene-1,4-dithiol, 3-hexyne-1,6-dithiol, p-phenylenedithiol, 1,4-bis-(α-mercaptomethyl)-benzene, 1,4-bis-(β-mercaptoethyl)-benzene, 1,4-bis-(γ-mercaptoethyl)-benzene and 1,5-dimercaptonaphthalene.

The dithiols used preferentially are the following:

1,6-Hexanedithiol, p-phenylenedithiol and 1,5-dimercaptonaphthalene.

(e) Coupling agents with different functional groups:

6-Hydroxy-caproic acid, 10-hydroxy-decanoic acid, 12-hydroxy-stearic acid, 6-amino-caproic acid, 9-aminononanoic acid, 11-amino-undecanoic acid, 12-amino-stearic acid, ethanolamine, 3-amino-propanol, 4-amino-butanol, 5-amino-pentanol, 6-amino-hexanol, 6-amino-5-methyl-1-hexanol, 10-amino-decanol, 4-p-aminophenyl-cyclohexanol, p-hydroxymethylbenzylamine, 4-hydroxymethyl-4'-aminomethyl-diphenyl, p-aminophenylethyl alcohol, N-β-aminoethyl-N-ω-hydroxyhexyl-aniline, 4-amino-thiophenol and monothioethylene glycol.

The compounds used preferentially are the following:
6-Hydroxy-caproic acid, 6-amino-caproic acid, ethanolamine and 4-p-aminophenyl-cyclohexanol.

3. To the formula B₃

By way of illustration, the compounds containing an anhydride group and an acid group may be mentioned:

Trimellitic anhydride, the 2:3 anhydride of 2,3,6-naphthalenetricarboxylic acid, the 1:2 anhydride of 1,2,5-naphthalenetricarboxylic acid, the 3:4 anhydride of 3,4,4'-diphenyltricarboxylic acid, the 3:4 anhydride of 3,4,3'-diphenylsulphonetricarboxylic acid, the 3:4 anhydride of 3,4,4'-diphenyl ether tricarboxylic acid, the 1:2 anhydride of 1,2,4-cyclopentadienetricarboxylic acid and the 3:4 anhydride of 3,4,4'-benzophenonetricarboxylic acid.

The compounds used preferentially are the following:
Trimellitic anhydride, the 1:2 anhydride of 1,2,5-naphthalenetricarboxylic acid, the 3:4 anhydride of 3,4,3'-diphenylsulphonetricarboxylic acid, the 3:4 anhydride of 3,4,4'-diphenyl ether tricarboxylic acid and the 3:4 anhydride of 3,4,4'-benzophenonetricarboxylic acid.

4. To the formula B₄

Amongst the dianhydrides which can be used there may be mentioned, by way of example, the following dianhydrides:

Ethylenetetracarboxylic dianhydride, methanetetracarboxylic dianhydride, 1:2, 3:4-butanetetracarboxylic dianhydride, 1:2, 4:5-pentanetetracarboxylic dianhydride, pyromellitic dianhydride, 1:6, 2:3-benzenetetracarboxylic dianhydride, 2:3, 2':3'-diphenyltetracarboxylic dianhydride, 3:4, 3':4'-diphenyltetracarboxylic dianhydride, 3:4, 3':4'-diphenylmethanetetracarboxylic dianhydride, 3:4, 3':4'-(2,2-diphenyl)-propanetetracarboxylic dianhydride, 3:4, 3'4'-diphenylsulphonetetracarboxylic dianhydride, 3:4, 3':4'-diphenyl ether tetracarboxylic dianhydride, 3:4, 3':4'-benzophenonetetracarboxylic dianhydride, 2:3, 6:7-naphthalenetetracarboxylic dianhydride, 1:2, 5:6-naphthalenetetracarboxylic dianhydride, 1:2, 4:5-naphthalenetetracarboxylic dianhydride, 1:8, 4:5-naphthalenetetracarboxylic dianhydride, 1:8, 4:5-decahydronaphthalenetetracarboxylic dianhydride, 1:2, 5:6-(4,8-dimethyl)-1,2,3,5,6,7-hexahydronaphthalenetetracarboxylic dianhydride, 1:8, 4:5-(2,6-dichloro)-naphthalenetetracarboxylic dianhydride, 1:8, 4:5-(2,7-dichloro)-naphthalenetetracarboxylic dianhydride, 1:8, 4:5-(2,3,6,7-tetrachloro)-naphthalenetetracarboxylic dianhydride, 1:10, 8:9-phenanthrenetetracarboxylic dianhydride, 3:4, 9:10-perylenetetracarboxylic dianhydride, 1:2, 3:4-cyclopentanetetracarboxylic dianhydride, 1:2, 4:5-cyclohexanetetracarboxylic dianhydride, 2:3, 4:5-pyrrolidinetetracarboxylic dianhydride, 2:3, 5:6-pyrazinetetracarboxylic dianhydride, 2:3, 4:5-thiophenetetracarboxylic dianhydride, cyclopentadienyltetracarboxylic dianhydride, 3:4, 3':4'-azoxybenzenetetracarboxylic dianhydride and 3:4, 3':4'-azobenzenetetracarboxylic dianhydride.

The dianhydrides used preferentially are the following:

Ethylenetetracarboxylic dianhydride, pyromellitic dianhydride, 2:3, 2':3'-diphenyltetracarboxylic dianhydride, 3:4, 3':4'-(2,2-diphenyl)-propanetetracarboxylic dianhydride, 3:4, 3':4'-diphenylsulphonetetracarboxylic dianhydride, 3:4, 3':4'-diphenyl ether tetracarboxylic dianhydride, 3:4, 3':4'-benzophenonetetracarboxylic dianhydride, 2:3, 6:7-naphthalenetetracarboxylic dianhydride and 1:2, 3:4-cyclopentanetetracarboxylic dianhydride.

II—NATURE OF THE ORGANO-SILICON COMPOUNDS (A) AND (A')

By way of illustration, the following compounds may be mentioned:

1-Amino-4-(vinyldimethylsilylmethoxy)-benzene, 1-hydroxy-4-(vinyldimethylsilylmethoxy)-benzene, 1-mercapto-4-(vinyldimethylsilylmethoxy)-benzene, 1-carboxy-4-(vinyldimethylsilylmethoxy)-benzene, 4-(vinyldimethylsilylmethoxy)-benzoic acid chloride, 1-methoxycarbonyl-4-(vinyldimethylsilylmethoxy)-benzene, 1-isocyanato-4-(vinyldimethylsilylmethoxy)-benzene, 1-amino-4-(2-vinyldimethylsilyl-ethoxy)benzene, 1-hydroxy-4-(2-vinyldimethylsilyl-ethoxy)-benzene, 1-amino-4-(3-vinyldimethylsilyl-propoxy)-benzene, 1-mercapto-4-(3-vinyldimethylsilyl-propoxy)-benzene, 1-amino-4-(vinyldimethylsilylmethoxycarbonyl)-benzene, 1-carboxy-4-(vinyldimethylsilylmethoxycarbonyl)-benzene, 1-amino-4-(vinyldimethylsilylmethylthio)-benzene, 1-ethoxycarbonyl-4-(vinyldimethylsilylmethylthio)-benzene, 1-ethoxycarbonyl-4-(vinyldimethylsilylmethylthiocarbonyl)-benzene, 1-ethoxycarbonyl-4-(vinyldimethylsilylmethylthio-thiocarbonyl)-benzene, 4-vinyldimethylsilylmethoxy-4'-aminodiphenylmethane, 4-vinyldimethylsilylmethoxy-4'-chlorocarbonyl-diphenylmethane, 4-vinyldimethylsilylmethoxy-4'-amino-diphenyl ether, 4-vinyldimethylsilyl-methoxy-4'-methoxycarbonyl-diphenyl ether, 4-vinyl-dimethylsilylmethoxy-4'-amino-diphenylsulphone, 4-vinyldimethylsilylmethoxy-4'-amino-diphenyl, 4-vinyl-dimethylsilylmethoxy-4'-hydroxy-diphenyl, 4-vinyl-dimethylsilylmethoxy-4'-chlorocarbonyl-diphenyl, 1-amino-4-(allyldimethylsilylmethoxy)-benzene, 1-amino-4-(but-1-enyl-dimethylsilylmethoxy)-benzene, 1-amino-4-(methyldivinylsilylmethoxy)-benzene, 1-amino-[(1,2,2-trichlorovinyl)-dimethylsilylmethoxy]-benzene, 1-amino- 4-(vinyldiphenylsilylmethoxy)-benzene, 1-amino-4-[vinyl-bis-(3,4-dichlorophenyl)-silylmethoxy]-benzene, 1-amino-4-(methylphenylvinylsilylmethoxy)-benzene, 1-amino-4-(methyl-γ-cyanopropylvinylsilyl-methoxy)-benzene, N-p-aminophenyl-N-vinyldimethyl-silylmethyl-methylamine, N-p-ethoxycarbonylphenyl-N-vinyldimethylsilylmethyl-methylamine, the ethyl ester of 4-(vinyldimethylsilylmethoxy)-butanoic acid, 4-vinyldimethylsilylmethoxy-butylamine, 3-amino-5-(vinyldimethylsilylmethoxy)-pyridine, 3-ethoxycarbo-nyl-5-(vinyldimethylsilylmethoxy)-pyridine, 1-amino-4-[(dimethylvinylsiloxy)-dimethylsilylmethoxy]-benzene, 1-aminomethyl-4-(vinyldimethylsilylmethoxy-benzene, 1-hydroxymethyl-4-(vinyldimethylsilylmethoxy)-benzene, the ethyl ester of 2-(vinyldimethylsilylmethyl)-thioglycolic acid, 1-amino-4-(methyl-γ-trifluoropropyl-vinylsilylmethoxy)-benzene and 4-(vinyldimethylsilyl-methoxy)-phthalic anhydride.

The unsaturated organo-silicon compounds of the formula (IV) are products which are particularly interesting because of the special reactivity conferred on them by the presence of the ethylenic double bonds, especially towards organo-silicon compounds containing hydrogenosilane groups. This property can be used advantageously—and this constitutes a further subject of the present invention—to obtain polymers containing fragments of organo-silicon chains and fragments of carbo-functional chains.

C. More particularly, a third subject of the present invention resides in thermoplastic polysiloxane elastomers containing carbo-functional units, obtained from the compounds of the formula (IV) in which n and n' are equal to 1.

The silicone rubbers have acquired considerable industrial importance because of their original chemical, physical and mechanical properties and especially because of their behaviour towards cold and heat. These elastomers are obtained by a long delicate process from elastomeric siloxane gums which are themselves in the form of more or less viscous products devoid of valuable mechanical properties. These gums are prepared by polymerization of cyclic siloxane oligomers or by polycondensation or copolycondensation of siloxane oligomers with terminal functional groups (for example alkoxy, hydroxyl and/or chlorine). The production of the silicone rubbers from polysiloxane gums requires firstly the preparation of masterbatches by incorporating into the gum various ingredients such as fillers (and especially silica in a great variety of forms), pigments and vulcanising agents, followed by the vulcanisation of these masterbatches, for example by heating in the presence of organic peroxides or, in the case of polysiloxane gums with terminal functional groups, by a cold treatment using polyfunctional crosslinking agents (silicates, trialkoxysilanes, triacetoxysilanes and the like). Regardless of the process employed, the vulcanisation, which makes it possible to convert a gum devoid of valuable mechanical properties to a rubber, must be preceded by the moulding of the desired objects because the vulcanised product is devoid of any thermoplasticity. On the other hand, the incorporation of fillers into the polysiloxane gums has proved indispensable; in effect, the silicone rubbers obtained by vulcanisation of unfilled gums have such low mechanical properties that they have not found any practical use. In certain cases the introduction of the fillers into the polysiloxane gums can have the effect of forming a mixture which is difficult to handle during the moulding process because of an interaction between the filler and the gum; it is then necessary to overcome this disadvantage by incorporating ingredients intended to minimise this interaction or to restore sufficient plasticity to the masterbatch. All these operations complicate the process of obtaining silicone rubbers and have proved costly from an economic point of view.

Attempts have been made to avoid the disadvantages referred to above whilst preserving the remarkable properties of silicone rubbers, by proceeding to develop thermoplastic elastomeric polymers. The method generally used to arrive at this objective consists of combining polysiloxane units and units of organic polycondensates in one polymeric chain. Thus it has been proposed, in U.S. Pat. No. 3,189,662, to obtain block copolycondensates containing polydiorganosiloxane units and units of polycarbonates of aromatic diols by reaction of an α-ω-dihalogenopolysiloxane with a diphenol in the presence of a halogen acceptor, to form an intermediate condensate which is then treated with phosgene. Although the polycondensate thus obtained is elastic, it has the disadvantage of containing, in its chain, Si—O—C bonds of which it is known that they are less stable to hydrolysis than the silicon-carbon bonds. It has also been proposed to prepare polymers containing polydiorganosiloxane units linked to one another by purely organic units via intermediate silicon-carbon bonds. Thus it has been proposed, in U.S. Pat. No. 3,176,034, to prepare copolymers containing a plurality of polydiorganosiloxane blocks linked to one another by organic units of the formula:

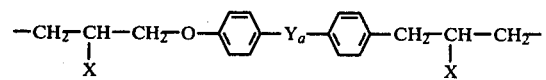

in which x is a halogen or hydrogen atom or a methyl radical, Y is an alkylene radical and a is 0 or 1, by reaction of an α,ω-dihydrogenopolydiorganosiloxane with allyl diethers of bisphenols in the presence of the usual hydrosilylation catalysts. The polymers thus obtained are "thermoplastic fluids" which must be converted by crosslinking when they are used. Ultimately it is found that no satisfactory solution has been provided to the problem of obtaining elastomeric thermoplastic polymers which simultaneously have the remarkable properties of silicone rubbers and excellent stability to hydrolysis. The subject of the invention resides precisely in the solution of this problem.

More precisely, the present invention provides polysiloxane thermoplastic elastomers, characterised in that they exhibit a plurality of recurring units of the general formula:

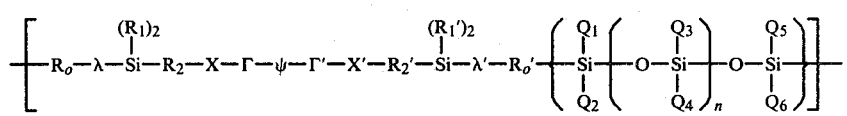 (XVII)

in which the various symbols have the following meaning:

$R_1$ and $R'_1$, $R_2$ and $R'_2$ and X and X' have the general or specific meanings given for the formula (I).

Γ and Γ' and Ψ have the general meanings given for the formula (IV).

$R_o$ and $R'_o$, which may be identical or different, represent divalent organic radicals containing from 2 to 10 carbon atoms.

λ and λ', which may be identical or different, denote a valency bond or one of the following organo-silicone groups:

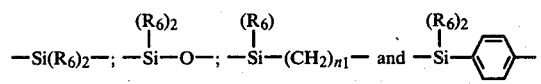

wherein $R_6$ and $n_1$ have the meaning already indicated.

$q_1$ to $Q_6$, which may be identical or different, are defined under $R_1$.

$n_3$ is a number ranging from 0 to 2,000.

More precisely, the various symbols shown in the formula (XVII) can assume the following particular meanings:

I-Radicals $R_1$ and $R'_1$; $R_2$ and $R'_2$; X and X'; T and T'

These can have all the specific meanings already mentioned for the formulae (I) and (IV).

II-Radicals G and G' and $G_1$ and $G'_1$

They can assume the more specific meanings given for the formulae (I) and (IV), with the restriction that if they are aliphatic or cycloaliphatic in nature, G and G' and $G_1$ and $G'_1$ do not contain double or triple carbon-carbon bonds.

III-Radical R''

It can assume the specific meanings given for the formula (IV) with the restriction that if R'' is aliphatic or cycloaliphatic in nature, it does not contain double or triple carbon-carbon bonds, and if it represents an aromatic radical it does not contain an alkenyl substituent. In the same way, the radicals $R_{10}$ and $R_{11}$ defined in connection with R'' represent only alkyl or phenyl radicals in the case of the compounds of the formula (XVII).

IV-Radicals R''' and R''''

They can assume the more specific meanings given for the formula IV except those which imply the presence of an ethylenic double bond.

V-Radicals $R_o$ and $R'_o$

These radicals represent a linear or branched alkylene group optionally substituted by 1 to 4 halogen atoms, especially chlorine and/or fluorine, or a cycloalkylene group optionally substituted by 1 to 4 atoms of halogen, especially of chlorine and/or fluorine.

More specifically, $R_o$ and $R'_o$ symbolise the following groups: ethylene; 1,3-propylene; 1,2-propylene; 1,4-butylene; 1,3-butylene; 2,3-butylene; 1,5-pentylene; 1,4-pentylene; hexamethylene; octamethylene; decamethylene; monochloroethylene; dichloroethylene; 1,2-difluoroethylene; 1,4-cyclohexylene; 1,3-cyclohexylene.

Preferably, $R_o$ and $R'_o$ represent linear alkylene groups containing from 2 to 6 carbon atoms.

VI-Radicals $Q_1$ to $Q_6$

They can preferably assume the specific meanings already mentioned for $R_1$.

VII-$n_3$ is preferably from 3 to 500.

Amongst the compounds of the formula (XVII), we claim more specifically those for which the various radicals of the said formula have the following meanings:

$R_o = R'_o$ is a linear alkylene radical having from 2 to 6 carbon atoms.

λ=λ' is a valency bond.

$R_1 = R'_1$ is an alkyl radical having from 1 to 6 carbon atoms optionally substituted by 1 to 4 atoms of chlorine and/or fluorine, or a phenyl, tolyl or xylyl radical optionally substituted by 1 to 4 atoms of chlorine and/or fluorine.

$Q_1$ to $Q_6$, which may be identical or different, have the same meaning as $R_1$.

$R_2 = R'_2$ is a methylene radical.

X=X' is an oxygen or sulphur atom or one of the radicals

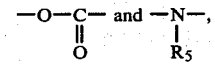

wherein $R_5$ is hydrogen or a methyl or ethyl group.

G=G' is an alkylene or alkylidene radical having from 1 to 6 carbon atoms; a cyclohexylene radical; a phenylene, tolylene, xylylene or benzylene radical; a radical formed by two phenylene groups linked to one another by a valency bond or by an alkylene or alkylidene group having from 1 to 4 carbon atoms; an oxygen atom; or one of the groups

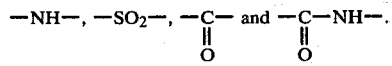

$G_1 = G'_1$ is a 1,2,4-benzenetriyl radical or one of the following radicals:

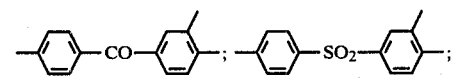

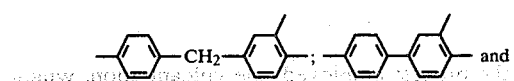

-continued

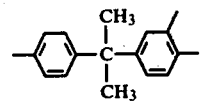

R″ represents an alkylene radical having from 1 to 8 carbon atoms; a cyclohexylene radical; a phenylene radical; a tolylene radical; a xylylene radical; or a divalent radical containing 2 to 4 phenylene groups linked to one another by a valency bond, by an oxygen atom or the groups

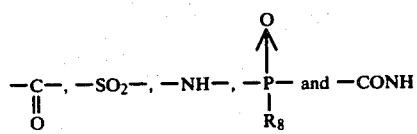

or by an alkylene or alkylidene group containing from 1 to 4 carbon atoms; a divalent radical containing 2 alkylene groups having from 1 to 4 carbon atoms linked to a phenylene group by a valency bond, by an oxygen atom or by one of the groups

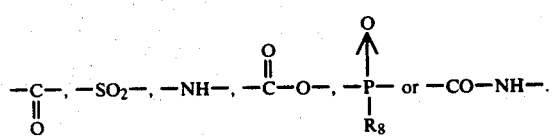

R‴ and R‴′ represent trivalent or tetravalent radicals containing 1 or 2 benzene nuclei linked to one another by a valency bond, an oxygen atom or a methylene radical; an isopropylidene radical; or one of the groups

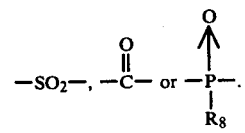

$n_3$ is from 10 to 200 and more particularly from 10 to 80.

T and T′ represent one of the groups

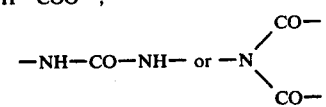

$\beta = \beta'$ is an oxygen atom.

As specific examples of compounds of the formula (XVII) there may be mentioned those which contain a plurality of recurring units of the formulae:

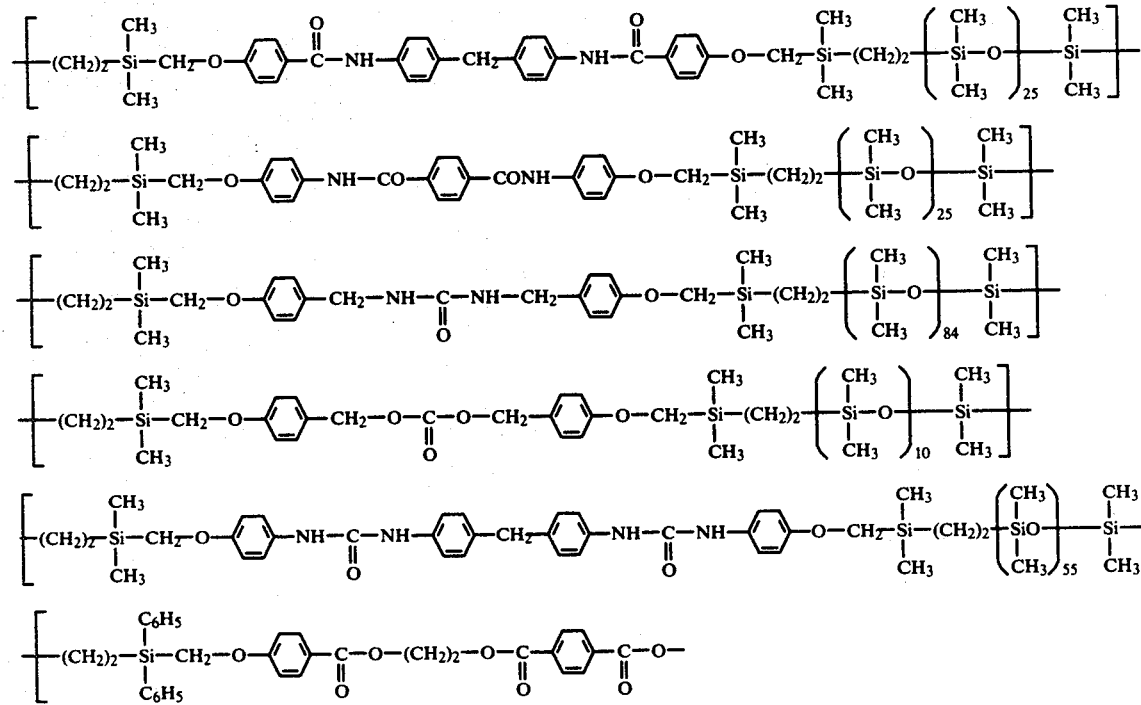

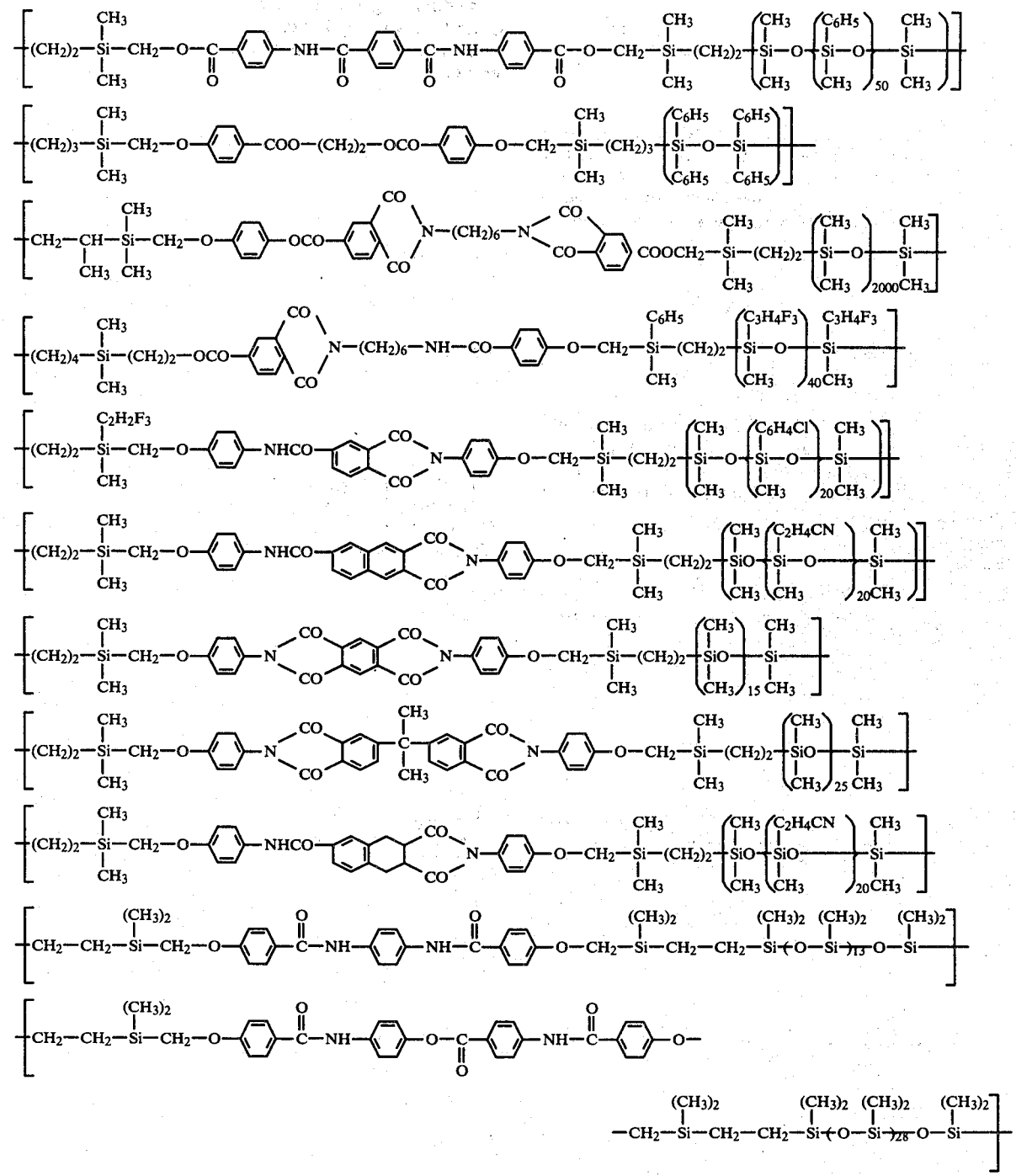

Preparation of the thermoplastic elastomers with recurring units of the formula (XVII)

The thermoplastic elastomers according to the invention can easily be obtained by reaction of at least one diethylenic silicon compound of the general formula:

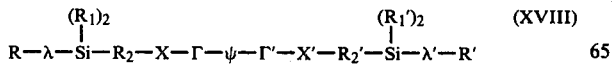

(XVIII)

in which R, R', λ, R$_1$, R$_2$, X, Γ, Ψ, Γ', X', R'$_2$, R'$_1$ and λ' have the meaning given above with the restriction that R and R' are only ethylenic hydrocarbon radicals with from 2 to 10 carbon atoms, with at least one α,ω-dihydrogenosiloxane of the general formula

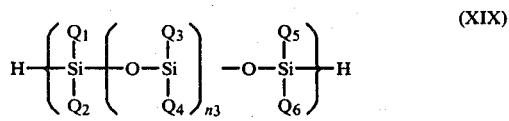

(XIX)

optionally in the presence of customary catalysts for the reaction of compounds having ≡Si—H groups with ethylenic double bonds. By way of example, this polyaddition reaction, which will hereafter be referred to as "hydrosilylation" can be illustrated by the following scheme if R and R' represent a vinyl group and λ and λ' represent a valency bond in the formula (XVIII):

supports such as carbon black, alumina and silica; catalysts of this type have in particular been described in U.S. Pat. No. 2,970,150. Another family of platinum catalysts consists of chloroplatinic acid (cf. U.S. Pat. No. 2,823,218) and the compounds derived therefrom, such as alkali metal chloroplatinates (cf. J. L. SPEIER, loc. cit.); and compounds obtained by reaction of chlo-

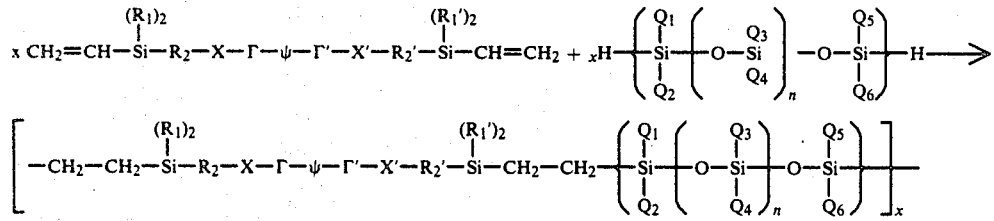

Conditions of the polyaddition reaction

The reaction of the compound (XVIII) with the compound (XIX) is carried out under the conditions usually employed during the addition of compounds having ≡Si—H groups with ethylenic compounds, cf. W. NOLL, Chemistry and Technology of Silicones (1968), pages 49 et seq.

Thus, the hydrosilylation reaction can be carried out by heating the reactants at, for example, 150° to 350° C. under autogenic pressure in the absence of catalysts. It can also be carried out in the presence of the customary catalysts, which makes it possible to use less high temperatures, of the order of 0° to 200° C., and allows the reaction to take place more rapidly under normal pressure.

As catalysts, compounds which generate free radicals are are suitably used, such as peroxidic compounds (for example acyl peroxides, alkyl peroxides and per-esters) or azo compounds. As illustrations of these compounds there may be mentioned benzoyl peroxide, acetyl peroxide, lauryl peroxide, t-butyl perbenzoate, t-butyl peracetate, t-butyl peroxide and N,N'-azo-bis-isobutyronitrile. The same effect is achieved if the process is carried out under ultraviolet irradiation instead of carrying out the reaction in the presence of catalysts which generate free radicals.

Another group of catalysts which can be employed to prepare the thermoplastic elastomers of the invention consists of the metals of group VIII of the periodic classification of the elements (cf. Handbook of Chemistry and Physics, 53rd edition) and their inorganic or organic derivatives. Amongst these metals there may in particular be mentioned Pt, Ru, Rh, Pd and Ir. The noble metals are particularly suitable, and platinum is very specially suitable. They can be used in the form of the element or in the form of salts or inorganic acids, in particular halides, salts of organic acids or complexes. Such catalysts have been described in the literature, cf., for example: U.S. Pat. Nos. 2,637,738 and 2,632,013; J. L. SPEIER et al., J. Am. Chem. Soc. 79, page 974 et seq. (1957); A. J. CHALK et al., J. Am. Chem. Soc. 87, 16 (1965).

Amongst these catalysts based on metals of group VIII, those based on platinum are very particularly suitable and are employed preferentially. They can assume various forms which are well-known in the technical literature. Thus, it is possible to use the various catalysts based on finely divided elementary platinum which may or may not be deposited on various roplatinic acid with alcohols, ethers or aldehydes (cf. U.S. Pat. No. 3,220,972), with olefines (cf. U.S. Pat. No. 3,159,601) or with cyclopropane (cf. U.S. Pat. No. 3,159,662). It is also possible to use the complexes of platinum halides with compounds which are donors of electron pairs, such as the phosphines, for example bis-(tributylphosphino)-dichloroplatinum (II) and bis-(triphenylphosphino)-dichloroplatinum (II) (cf. A. J. CHALK et al., loc. cit.). Elementary platinum deposited on charcoal and chloroplatinic acid and its derivatives are the platinum catalysts used preferentially.

The hydrosilylation reaction can be carried out in the absence of a solvent or by bringing the reactants and, if appropriate, the catalyst, into contact in an organic medium consisting of a solvent or a diluent which is inert under the reaction conditions. As such there may especially be used saturated aliphatic hydrocarbons such as pentane, hexane and heptane; saturated cycloaliphatic hydrocarbons such as cyclohexane; aromatic hydrocarbons, such as benzene and toluene; halogenated hydrocarbons such as chloroform, dichloroethane and chlorobenzene; alcohols such as ethanol, propanol and isopropanol; ethers, such as tetrahydrofurane; and esters, such as methyl acetate, ethyl acetate and butyl acetate. The choice of the reaction medium depends on the nature of the starting reactants and on the temperature at which the reaction takes place. The reaction can take place in solution or in suspension depending on whether one or both reactants are soluble or insoluble in the chosen medium.

The relative amounts of the compounds of the formula (XVIII), which will hereafter be referred to as "dialkenylsilane monomer" or "dialkenylsilane" and of the α,ω-dihydrogenopolysiloxane, which will hereafter be referred to as "dihydrogeno monomer", can vary within wide limits. Thus, the relative amount of the reactants, expressed by the ratio of the number of alkenyl groups introduced by the dialkenylsilane monomer to the number of active hydrogen atoms introduced by the dihydrogeno monomer can vary for example from 2 to 0.5. However, to obtain polymers of high molecular weight it is preferable that the ratio defined above should be close to 1, though a slight excess of one or other of the reactants can be used. Thus the ratio of alkenyl group/H is preferably from 1.2 to 0.8. In this case the molecular weight of the thermoplastic elastomer of the invention can, where necessary, be adjusted to the desired value by using a chain stopper consisting of a silicon compound containing a single ≡Si—H group or consisting of an organic or organo-silicon compound containing only one ethylenic double bond.

Though any compound having a≡Si—H group can be used as the chain stopper, the following should be mentioned particularly: trimethylsilane, triethylsilane, tri-n-propylsilane and diethylmethylsilane.

Amongst the chain stoppers having an alkenyl group, organo-silicon compounds such as trimethylvinylsilane, triethylvinylsilane and allyltrimethylsilane are used preferentially, though it is possible, to use organic mono-unsaturated compounds such as vinyl acetate, styrene or allylbenzene.

The amount of chain stopper is decided as a function of the desired molecular weight of the thermoplastic elastomer, in accordance with the rules well-known in polymer chemistry to those skilled in the art.

If a catalyst is used to carry out the hydrosilylation reaction, the amount employed can vary within very wide limits depending on the nature of the catalysts, the nature of the reactants employed and the reaction conditions. Where a compound which generates free radicals is used, it is possible to use, for example, from $1 \times 10^{-4}$ to 0.1 mol of catalyst per mol of dialkenylsilane monomer, though it is possible, without disadvantage, to go outside these limits. If the catalyst is one of the abovementioned metals or a derivative of these metals, especially platinum, the amount of catalyst, expressed as gram atoms of metal per alkenyl group present in the dialkenyl monomer is suitably from $10^{-6}$ to $10^{-1}$ gram atom of metal per alkenyl group and preferably from $10^{-5}$ to $10^{-2}$.

As has already been indicated, the reaction temperature can vary within wide limits depending on whether the reaction is carried out in the presence or absence of a catalyst or, in the former case, depending on the nature and amount of catalyst employed. Overall, the temperature can vary eg. from 0° to 300° C. and preferably from 20° to 250° C. The use of platinum catalyst makes it possible to work at temperatures of the order of 10° to 200° C. The reaction can also be carried out at a pressure above, below or equal to atmospheric pressure.

To prepare the thermoplastic elastomers of the formula (XVII), in which R" is an arylene radical containing one or more functional groups such as specified earlier, it is preferable to employ compounds of the formula (XVIII), in which the functional groups carried by the arylene radicals R" are inert towards the dihydrogenosiloxane under the reaction conditions. To obtain compounds of the formula (XVII) in which R" represents an arylene radical substituted by a functional group capable of reacting with the dihydrogenosiloxane (for example an amine group), a compound of the formula (XVIII) is employed, in which the functional group or groups carried by the arylene groups R" are blocked by inert groups and are then liberated by treating the polymer obtained after hydrosilylation (for example by hydrogenation of nitro groups to amine groups, in a known manner).

As specific examples of dialkenylsilane monomers of the formula XVIII which can be employed for the preparation of the thermoplastic silicon-based elastomers there may be mentioned specifically those represented by the formulae (1), (2), (3), (4), (5), (6), (7), (8), (9), (10), (11), (12), (13), (14), (15), (16), (18), (19), (20), (21), (22) and (23).

The α-ω-dihydrogenopolysiloxanes of the formula (XIX) employed as comonomers for the preparation of the thermoplastic elastomers are known products obtained in accordance with the usual processes of the chemistry of the silicones. For example, it is possible to hydrolyse the monohalogenodiorganosilane, such as monochlorodimethylsilane, or cohydrolyse a monohalogenodiorganosilane, a dihalogenodiorganosilane and/or a cyclic polydiorganosiloxane such as octamethylcyclotetrasiloxane; it is also possible to react a monohalogenodiorganosilane with an α,ω-dihydroxypolysiloxane of a variety of molecular weights or an α,ω-dialkoxypolysiloxane; further, it is possible to react a dihydrogenodiorganosiloxane with an α,ω-dihydroxypolysiloxane or an α,ω-dihalogenodiorganosiloxane with a metal hydride such as lithium aluminium hydride.

They can also be obtained by cationic polymerisation of an octaorganocyclotetrasiloxane such as octamethylcyclotetrasiloxane with an α,ω-dihydrogenomonosiloxane such as α,ω-dihydrogenotetramethylsiloxane.

The molecular weight of the α,ω-dihydrogenosiloxane of the formula (XIX) is determined by the value of n, which can vary between 0 and 2,000. In general, compounds in which n is from 3 to 500 and preferably from 10 to 200 and especially from 10 to 80 are used.

The α,ω-dihydrogenopolysiloxane can be a homopolysiloxane or a copolymer derived from two or more dihalogenodiorganosiloxanes. The copolymers can be either compounds in which the various units are arranged as random or block copolymers.

As specific examples of compounds of the formula (XIX) there may be mentioned: dihydrogenotetramethyldisiloxane, dihydrogenodiethyldimethyldisiloxane, dihydrogenodiphenyldimethyldisiloxane or the compounds of the formula:

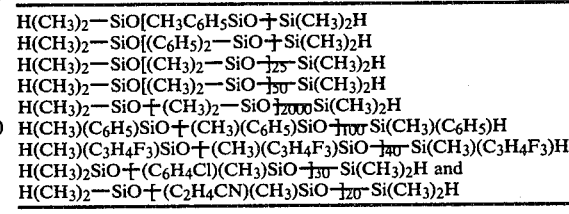

To prepare the thermoplastic elastomers according to the invention it is possible, as has already been mentioned above, to employ one or more dialkenylsilane monomers (XVIII) together with one or more α,ω-dihydrogenopolysiloxanes (XIX). In the latter case it is possible to react 2 or more than two monomers (XVIII) or (XIX). This gives copolymeric thermoplastic elastomers. It is also possible to obtain block copolymers by reacting a thermoplastic elastomer containing a plurality of recurring units of the formula (XVII) and having, at each end of the chain, a monoalkenylsilane unit or a hydrogenosiloxane unit, with a thermoplastic elastomer containing a plurality of recurring units of the formula (XVII) different from those of the first elastomer and terminated by hydrogenosiloxane or monoalkenylsilane unit, respectively.

The thermoplastic elastomers according to the invention can be used in all the fields where silicone elastomers are conventionally used, as they retain the properties of the latter, but also in other fields which are those where thermoplastic polymers are used because of the ease with which they may be employed. They can be converted into various moulded articles by extrusion or injection in the molten state, or by stamping. They are particularly suitable for the production of films or of fibres. They can also be converted into finished articles by starting from their solutions in organic solvents.

Before being used, the thermoplastic elastomers according to the invention can be mixed with the usual additives such as pigments, fillers such as the various types of silica, titanium oxide and carbon blacks, plasticisers or heat stabilisers and light stabilisers.

The examples which follow illustrate the invention and show how it can be put into practice; all temperatures are given in degrees Centigrade.

EXAMPLE 1

64.4 g of sodium p-nitrophenate are dissolved in 203 g of N-methylpyrrolidone and this solution is introduced into a flask. After heating to 90° C., 53.8 g of dimethylvinylchloromethylsilane are run in over the course of 13 minutes and 10 cm$^3$ of N-methylpyrrolidone are added. The reaction mixture is kept at about 100° for 20 hours, the sodium chloride is filtered off and the N-methylpyrrolidone is distilled under reduced pressure. The residual reaction mixture is dissolved in ether and the ether solution is washed with an aqueous sodium carbonate solution. After distilling the ether, 91 g of a yellow product crystallising at 34° are obtained. The percentage analysis and infra-red analysis show that the compound is p-(dimethylvinylsilylmethoxy)-nitrobenzene.

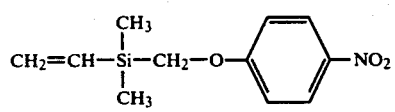

EXAMPLE 2

102.8 g of p-aminobenzoic acid and 500 cm$^3$ of N-methylpyrrolidone are introduced into a flask and after the material has dissolved 60.7 g of triethylamine are introduced at 25°. 67.4 g of vinyldimethylchloromethylsilane are then run in, over the course of 3 hours, into the mixture heated to 130°. The whole is kept at 130° for 21 hours and after cooling 64.8 g of triethylamine hydrochloride are filtered off.

The N-methylpyrrolidone is removed by distillation and the distillation residue is taken up in 200 cm$^3$ of ether and then washed with an aqueous sodium carbonate solution. The ether is removed by distillation and after rectification a fraction weighing 78.8 g, of boiling point$_{0.35}$: 153°–154°, which corresponds to p-(dimethylvinylsilylmethoxycarbonyl)-aminobenzene, is obtained. The IR spectrum, the determination of the amine groups and the microanalysis are in agreement with the formula:

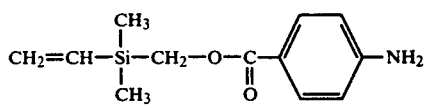

p-(Dimethylvinylsilylmethoxycarbonyl)-aminobenzene crystallises at 30°.

EXAMPLE 3

760 g of methyl p-hydroxybenzoate and 850 ml of N-methylpyrrolidone are introduced into a flask and a methanolic solution of sodium methylate, prepared from 960 g of methanol and 115 g of sodium, is run in over the course of 2 hours 20 minutes at between 82° and 100°. The methanol is then removed by distillation and 672 g of vinyldimethylchloromethylsilane are run over the course of 1 hour 5 minutes at between 108° and 128°.

After distilling the N-methylpyrrolidone, the distillation residue is taken up with 2 l of cyclohexane and washed with water, and the methyl p-(dimethylvinylsilylmethoxy)-benzoate is rectified. This gives 1,136 g of a fraction of boiling point$_{0.1}$: 110°–113°, having a melting point of 25.5°.

Treatment of the methyl p-(dimethylvinylsilylmethoxy)-benzoate with a sodium hydroxide solution containing 100 g of sodium hydroxide, 250 g of water and 1,000 ml of methanol gives the sodium salt of p-(dimethylvinylsilylmethoxy)-benzoic acid.

After acidifying a solution containing the sodium salt of p-(dimethylvinylsilylmethoxy)-benzoic acid, a white product melting at 118° is isolated by filtration; it corresponds to p-(dimethylvinylsilylmethoxy)-benzoic acid:

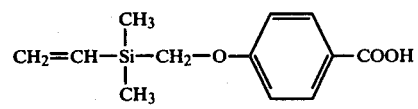

EXAMPLE 4

354 g of p-(dimethylvinylsilylmethoxy)-benzoic acid, prepared in accordance with the procedure described in Example 3, are introduced into a flask and 357 g of thionyl chloride are run in over the course of 40 minutes at between 28° and 29°. The reaction mixture is then heated and kept at 102° for 1 hour. Rectification gives a fraction of 344 g, of boiling point$_{0.1}$ 126°–127°, corresponding to the chloride of p-(dimethylvinylsilylmethoxy)-benzoic acid:

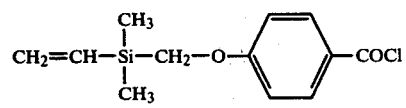

EXAMPLE 5

26.5 g of sodium are introduced gradually into a flask containing 224 g of methanol and this solution is run, over the course of 50 minutes, into another flask containing 175 g of methyl p-hydroxybenzoate and 200 ml of N-methylpyrrolidone. Whilst this material is being run in, the methanol is distilled. When the addition is complete, 171 g of allyldimethylchloromethylsilane are introduced over the course of 7 minutes, the reaction mixture being kept at 100°. After rectification, a fraction of 215 g corresponding to methyl p-(dimethylallylsilylmethoxy)-benzoate is obtained:

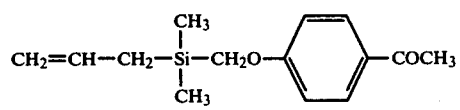

The sodium salt of p-(allyldimethylsilylmethoxy)-benzoic acid, and p-(allyldimethylsilylmethoxy)-benzoic acid itself (melting point=93° C.) are prepared according to a process analogous to that described in Example 3.

EXAMPLE 6

25.2 g of ethyl thioglycollate and 100 ml of methanol are introduced into a flask and 41.7 ml of sodium methylate (a 4.8 M solution in methanol) are run in over the course of 15 minutes at 20°. 26.94 g of dimethylvinylchloromethylsilane are then added over the course of 5 minutes, after which the methanol is distilled. After filtering the sodium chloride and rectifying the filtrate, a fraction of 43.2 g, of boiling point$_1$: 86°–88° is obtained, which corresponds to ethyl (vinyldimethylsilyl)-methylmercaptoacetate:

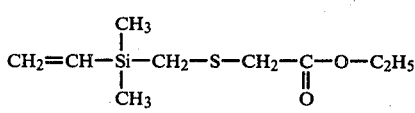

EXAMPLE 7

775 g of stannous chloride and 700 g of hydrochloric acid (d=1.19) are introduced into a flask and a solution of p-(vinyldimethylsilylmethoxy)-nitrobenzene prepared according to the procedure of Example 1 and containing 118.5 g of the nitro derivative and 150 cm$^3$ of ethanol is then run in over the course of 50 minutes at between 30° and 45°.

The reaction mixture is kept at 45° for 2 hours. After cooling, the following are carried out: filtration of the tin tetrachloride, washing with water, neutralisation with a concentrated sodium hydroxide solution and filtration of the precipitate formed. This precipitate is dissolved in excess sodium hydroxide solution.

After extracting with ether, removing the ether by evaporation, and rectification, a fraction, 79.8 g, of boiling point$_{0.8}$: 115°–117°, of p-(vinyldimethylsilylmethoxy)aminobenzene is obtained:

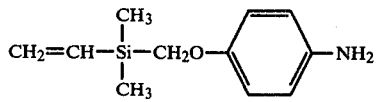

EXAMPLE 8

34.7 g of xylene, 0.4 g of tetramethylurea and 16.15 g of phosgene are introduced into a flask, the mixture is heated under reflux and a solution consisting of 30.6 g of p-(dimethylvinylsilylmethoxy)-aminobenzene, prepared in accordance with the method described in Example 2, and 34.7 g of xylene, is run in over the course of 30 minutes. The reaction mixture is kept at the reflux temperature throughout the addition. Thereafter, heating under reflux is continued for 30 minutes.

Rectification under reduced pressure gives 28 g of a colourless oil of boiling point$_{0.2}$=110°, corresponding to 1-isocyanato-4-(dimethylvinylsilylmethoxy)-benzene:

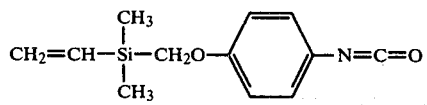

EXAMPLE 9

91.5 g (0.6 mol) of methyl p-hydroxybenzoate and 100 cm$^3$ of methanol are introduced into a 500 cm$^3$ flask equipped with a mechanical stirring system, a dropping funnel, a reflux condenser, a thermometer and a heating device.

The contents of the flask are heated to the reflux temperature and a solution of 24 g of NaOH in 200 cm$^3$ of methanol is added over the course of 40 minutes. Thereafter, the methanol is removed by distillation and 200 cm$^3$ of N-methylpyrrolidone are added. The contents of the flask are heated to 113°–127° C. and 88 g of methyldivinylchloromethylsilane are added. The mixture is kept under these conditions for 1 hour 30 minutes.

The N-methylpyrrolidone is then driven off by distillation. The residue is taken up in 250 cm$^3$ of cyclohexane and this solution is thereafter washed with water, and then distilled. 146 g of a product having the following characteristics are thus isolated:

| Boiling point/0.5 mm Hg | 125–130° C. |
|---|---|
| Melting point | 18° C. |
| n$_{20}$$^D$ | 1.532 |
| d 20/4 | 1.0525 |

The percentage analysis of the product is as follows:

| C % | = 63.07 |
|---|---|
| H % | = 6.94 |
| Si % | = 10.7 |
| Vinyl % | = 20.6 |

The infra-red spectrum corresponds to that of methyl p-(divinylmethylsilylmethoxy)-benzoate.

EXAMPLE 10

The sodium salt of p-(divinylmethylsilylmethoxy)-benzoic acid is prepared by treating 105 g of methyl p-(divinylmethylsilylmethoxy)-benzoate with a solution of 20 g of NaOH in 50 cm$^3$ of water and 200 cm$^3$ of methanol. After acidification, a white product (98 g) of melting point 104° C. is isolated by filtration; its percentage composition is as follows:

| C % = | 62.05 |
|---|---|
| H % = | 6.37 |
| Si % = | 10.56 |
| Vinyl % = | 21.24 |

The compound is identified as being p-(divinylmethylsilylmethoxy)-benzoic acid.

74.5 g of the acid obtained above are introduced into the apparatus described in Example 9 and 71.5 g of thionyl chloride (0.6 mol) are added over the course of 15 minutes at between 25° and 28° C. The reaction mixture is then kept at the reflux temperature for 1 hour. Distillation gives 74 g of a fraction which passes over at between 117° and 120° C. under 0.06 mm of mercury. This product was identified as being the chloride of p-(divinylmethylsilylmethoxy)-benzoic acid. Its melting point is 22° C.

EXAMPLE 11

Preparation of the compound (3)

10.35 g of 1-amino-4-(vinyldimethylsilylmethoxy)-benzene (compare Example 7), 5.05 g of triethylamine and 50 cm³ of carbon tetrachloride are introduced into a three-neck 250 cm³ flask equipped with a mechanical stirrer, a reflux condenser, a dropping funnel and a thermometer, the whole being kept under an atmosphere of dry nitrogen.

The reaction mixture is cooled to −4° C. whilst stirring. A solution of 5.22 g of terephthaloyl chloride in 17 cm³ of acetone is introduced into the dropping funnel and is then run in uniformly over the course of 27 minutes. During the addition, the temperature is kept at between −4° and +2° C. The reaction mixture is left for a further 1 hour 30 minutes, whilst being stirred vigorously.

Thereafter, the reaction mixture is poured into 100 cm³ of water; the precipitate formed is filtered off, washed with 4 times 40 cm³ of a mixture of water and acetone, again filtered off and then dried at 110° C. under reduced pressure (5 mm Hg).

This gives 12.90 g of a product of melting point (Kofler) 315° C.

The following analyses are carried out on the isolated product:

| percentage analysis: | |
|---|---|
| C % = | 66.09 |
| H % = | 6.53 |
| N % = | 5.06 |

NMR spectrum: the ratio of the protons of the vinyl group and the aromatic protons is in accordance with theory.

IR spectrum: the following different absorption bands are observed:

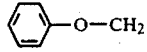

| Si—CH=CH₂ | 1,010 and 950 cm⁻¹ |
|---|---|
| Si—CH₃ | 1,250–830 cm⁻¹ |
| NH | 3,280 cm⁻¹ |
| CO | 1,640 cm⁻¹ |
| CO⟨phenyl⟩—O—CH₂ | 1,230 and 1,110 cm⁻¹ |

EXAMPLE 12

(1) Preparation of the compound (4)

65.5 g of 4,4′-diamino-diphenylmethane dissolved in 350 ml of anhydrous chloroform and 74 g of triethylamine are introduced into a 500 cm³ three-neck flask equipped as in Example 11.

The reaction mixture is cooled to 0° C. whilst stirring. 168 g of the chloride of p-(dimethylvinylsilylmethoxy)-benzoic acid are run in over the course of 1 hour 30 minutes. During the addition the temperature is kept at 0°≃1° C.

The solution is then run into 400 cm³ of water whilst stirring. The organic layer is separated off, washed with 3 times 200 cm³ of water, dried over anhydrous magnesium sulphate and then evaporated to constant weight. This gives 219 g of a crude product which is treated with 10 g of charcoal and recrystallised from 500 cm³ of absolute ethanol.

171 g of 4,4′-N,N′-bis-[p-(vinyldimethylsilylmethoxy)-benzoyl]-diaminodiphenylmethane, of melting point 154° C., are isolated in this way.

The following analyses are carried out on the isolated product:

| percentage analysis: | |
|---|---|
| C % | 69.90 |
| H % | 6.76 |
| N % | 4.58 |
| Si % | 8.75 |

NMR spectrum: in agreement with formula (4). determination of free amine groups: this determination proves negative.

EXAMPLE 13

Preparation of the compounds (17) and (18)

41.4 g of 1-amino-4-(vinyldimethylsilylmethoxy)-benzene prepared in accordance with the method described in Example 7, and 100 cm³ of dimethylformamide containing 0.02% of water, are introduced into a 500 cm³ three-neck flask equipped as in Example 11.

The reaction mixture is heated to 60° C. whilst stirring and 21.8 g of pyromellitic anhydride are added gradually over the course of 20 minutes, in small fractions of 3 g.

A limpid yellow solution of the compound (17) is obtained.

Stirring, and heating at 60° C., is continued for a further hour, 30.6 g of acetic anhydride are added over the course of 5 minutes and 6.2 cm³ of pyridine are then run in over the course of 5 minutes. As from the end of the addition of the pyridine, a yellow precipitate forms. Heating is continued for 1 hour 45 minutes, the temperature being kept at between 60° and 70° C.

After cooling, the precipitate formed is filtered off, washed with 4 times 40 cm³ of acetone, suction-drained and dried at about 110° C. under reduced pressure (25 mm Hg) for 8 hours.

50.2 g of a crude product are obtained, and a 45 g portion is recrystallised by dissolving in 2,000 cm³ of dimethylformamide at the boil.

43.1 g of yellow crystals melting at 380° C., with decomposition, are obtained.

The following analyses are carried out on the recrystallised product:

| percentage analysis: | |
|---|---|
| C % | 64.42 |
| H % | 5.60 |
| N % | 4.79 |

| IR spectrum | |
|---|---|
| CO | 1,785–1725 cm⁻¹ |
| Si—CH=CH₂ | 1,010 and 960 cm⁻¹ |
| Si—(CH₃)₂ | 860 and 800 cm⁻¹ | thin layer chromatography (TLC): a spot with Rf=0.62 is obtained by chromatography on a silica plate, the eluant being a mixture of ethyl acetate (90%) and benzene (10%).

EXAMPLE 14

Preparation of the compound (5)

41.4 g of 1-amino-4-(vinyldimethylsilylmethoxy)-benzene synthesised as in Example 1 and 50 cm³ of dimethylformamide are introduced into a 500 cm³ three-neck flask equipped as in Example 11.

The mixture is stirred and a solution of 25 g of 4,4'-diisocyanato-diphenylmethane in 75 cm³ of dimethylformamide is run in slowly over the course of 30 minutes. During the addition, the temperature of the reaction mixture is kept at between 7° and 13° C.

The heating is then continued for 3 hours at 20°-22° C. The colourless solution is then run, whilst stirring, into 400 cm³ of iced distilled water. After allowing the phases to separate for 2 hours, the precipitate is filtered off and then washed with 5 times 75 cm³ of water.

54 g of a crude product are obtained and are purified by dissolving in 200 cm³ of dimethylformamide and treating with 200 cm³ of acetonitrile so as to bring about the precipitation. The mixture is cooled for 2 hours in an ice bath and the precipitate is filtered off, then washed with 300 cm³ of acetonitrile, suction-drained and dried at 110° C. under 1 mm Hg for 8 hours.

53 g of a white product which melts at 280° C., with decomposition, are obtained.

The following analyses are carried out on the precipitated product:

| percentage analysis: | |
|---|---|
| C % | 66.65 |
| H % | 6.65 |
| N % | 8.42 |

| IR spectrum: | |
|---|---|
| NH | 3,300 cm⁻¹ |
| CO | 1.665 cm⁻¹ |
| Si—CH=CH₂ | 1,010 and 960 cm⁻¹ |
| Si—(CH₃)₂ | 830 cm⁻¹ |
| 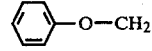—O—CH₂ | 1,220 cm⁻¹ |

TLC: a spot of Rf=0.87 is obtained, the elution solvent being a mixture of chloroform (96%) and methanol (4%).

EXAMPLE 15

Preparation of the compound (6)

6.36 g of ethylene glycol terephthalate and 30 cm³ of pyridine are introduced into the apparatus previously described in Example 11.

This solution is cooled to about 5° C. and 12.74 g of the chloride of p-(dimethylvinylsilylmethoxy)-benzoic acid synthesised as in Example 3, are introduced in small fractions over the course of 12 minutes.

The temperature of the reaction mixture rises to 10° C. at the end of the addition. The heating of the solution is increased progressively, the solution becoming limpid at about 76° C., and is continued at 110° C. for 3 hours.

The mixture is cooled whilst stirring. A copious precipitate of pyridine hydrochloride forms, which is filtered off, washed with twice 5 cm³ of anhydrous pyridine and then suction-drained. The filtrate is poured into 300 cm³ of iced water, whilst stirring. After allowing the phases to separate for 1 hour, the precipitate is filtered off, then washed with 300 cm³ of water, suction-drained and dried.

This gives 16.4 g of white crystals melting at 70° C., which are then recrystallised from 100 cm³ of isopropanol. After filtration and drying, 14.6 g of white crystals melting at 72°-74° C. are obtained.

The following analyses are carried out on the recrystallised product:

| percentage analysis: | |
|---|---|
| C % | 62.76 |
| H % | 6.53 |
| Si % | 7.69 |

| IR spectrum: | |
|---|---|
| CO | 1,730 and 1,710 cm⁻¹ |
| | 1,250 cm⁻¹ |
| ⌬—O—CH₂ | |
| Si—CH=CH₂ | 1,020 and 965 cm⁻¹ |
| Si—CH₃ | 830 cm⁻¹ |

TLC: a spot of Rf=0.44 is obtained, the eluant being benzene.

EXAMPLE 16

Preparation of the compound (7)

20 g of 1-amino-4-(vinyldimethylsilylmethoxycarbonyl)-benzene, 8.6 g of triethylamine and 50 cm³ of acetone are introduced into the apparatus previously described in Example 11.

A solution of 8.8 g of terephthaloyl chloride dissolved in 100 cm³ of acetone is introduced into the dropping funnel and is then run into the reaction mixture, kept at 35° C. After adding 11 cm³ of the solution of terephthaloyl chloride, a white precipitate forms.

The addition is continued and lasts for 1 hour 15 minutes.

The reaction mixture is then brought to the boil and kept at its boiling point, namely 58° C., for 1 hour.

After cooling, the precipitate is filtered off on a glass frit and is then washed with 5 times 50 cm³ of water, suction-drained and then dried for 4 hours at 100° C. under 25 mm pressure.

21.2 g of product are thus obtained.

The filtrate is precipitated by 500 cm³ of water, which makes it possible to obtain a further 3.57 g of product.

10 g of product originating from the first filtration are recrystallised from 250 cm³ of chlorobenzene, making it possible to obtain 8.9 g of pearlescent crystals identified as being N,N'-bis-p-[(vinyldimethylsilyl)methoxycarbonyl)-phenyl]-terephthalamide of melting point 260° C.

The following analyses are carried out on the purified product:

| percentage analysis: | |
|---|---|
| C % | 64.38 |
| H % | 6.06 |
| N % | 4.97 |
| Si % | 9.1 |

NMR spectrum: in agreement with formula (7).

IR spectrum:

| | |
|---|---|
| CO (conjugated ester) | 1,700 cm$^{-1}$ |
| CO (secondary amide) | 1,665 cm$^{-1}$ |
| NH | 3,350 cm$^{-1}$ |
| C—NH | 1,530 cm$^{-1}$ |
| Si—CH$_3$ | 1,250 cm$^{-1}$ |
| Si—CH=CH$_2$ | 1,010 cm$^{-1}$ and 955 cm$^{-1}$ |
| aromatic disubstitution and Si—(CH$_3$)$_2$ | 830–850 cm$^{-1}$ |

EXAMPLE 17

(1) Preparation of the compound (19)

4.25 g of 1,3-bis-(3-p-aminophenoxy-propyl)-tetramethyldisiloxane, 1.84 g of triethylamine and 50 cm$^3$ of acetone are introduced into a 100 cm$^3$ three-neck flask equipped as in Example 11.

4.63 g of the chloride of p-(dimethylvinylsilylmethoxy)-benzoic acid prepared in accordance with the procedure of Example 3 and 30 cm$^3$ of acetone are introduced into the dropping funnel.

The reaction mixture is stirred and cooled to 3° C.

Thereafter, the solution of the acid chloride is run in over the course of 15 minutes. The temperature rises to 6° C. at the end of the addition.

Thereafter, the reaction mixture is heated to 50° C. and this temperature is maintained for 1 hour.

After cooling, the reaction mixture is poured into one liter of water, whilst stirring. The precipitated formed is filtered off, washed with 100 cm$^3$ of water and then dried.

7.43 g of a crude product are obtained.

6 g of this compound are recrystallised from 200 cm$^3$ of methanol.

5.1 g of a whitish solid of melting point 145° C. are collected.

3.25% of nitrogen and 7.53% of hydrogen are found by elementary analysis.

TLC gives a single spot of Rf=0.74, the eluant being a mixture of toluene (90%) and ethyl acetate (10%).

(2) Preparation of 1,3-bis-(3-p-aminophenoxy-propyl)tetramethyldisiloxane

The coupling agent is synthesised as follows:

66 g of 4-allyloxy-nitrobenzene and 0.07 cm$^3$ of a solution of chloroplatinic acid in alcohol, containing 30 mg of platinum/cm$^3$, are introduced into a 250 cm$^3$ three-neck flask equipped with a mechanical stirrer, a condenser, a dropping funnel and a thermometer, the whole being kept under an atmosphere of nitrogen.

25 g of tetramethyl-1,3-dihydrogenodisiloxane are introduced into the dropping funnel and the addition of 5 cm$^3$ to the reaction mixture is started, whilst stirring at ambient temperature. The reaction mixture is then heated to about 100° C. and the addition is continued; the temperature rises sharply to about 200° C. The reaction mixture is cooled to 130° C. and this temperature is maintained for 30 minutes.

After cooling, a viscous mass is obtained, which is run, whilst stirring, into 2,000 cm$^3$ of ethanol.

A precipitate forms, which is filtered off and dried.

18.8 g of a compound melting at 80° C., on which the following analyses are carried out, are obtained:

IR spectrum:

| | |
|---|---|
| ⟨phenyl⟩—NO$_2$ | 1,510–1,330 cm$^{-1}$ |
| Si—CH$_3$ | 1,250 cm$^{-1}$ |
| | 1,265 cm$^{-1}$ |
| ⟨phenyl⟩—O—CH$_2$ | |
| Si—O | 1,080 cm$^{-1}$ |

NMR spectrum: in accordance with theory.

The reduction of the nitro group is carried out in the following manner:

10 g of the compound prepared above, 50 cm$^3$ of ethyl acetate and 0.2 g of ADAMS platinum containing 83.6% of platinum are introduced into a 125 cm$^3$ stainless steel autoclave.

The autoclave is flushed with nitrogen. Hydrogen under a pressure of 50 bars is introduced into the reaction mixture which is kept at ambient temperature. After 15 minutes, the pressure drops to 28 bars and the initial pressure is re-established.

After 35 minutes, the mixture is heated to 55° C. for 1 hour.

After cooling the autoclave, a catalyst suspension is obtained, which is then separated by filtration.

The solvent is evaporated under reduced pressure.

9.15 g of an amine liquid are obtained, containing 0.0392 mol of amine group according to determination by means of perchloric acid.

TLC on a silica plate, the elution solvent being ethyl acetate, gives a spot of Rf=0.34.

EXAMPLE 18

Preparation of the compound (20)

45 g (0.1 M) of bis-(4-amino-4'-benzamido-phenyl)-methane, followed by 250 cm$^3$ of N-methylpyrrolidone, are introduced into a 500 cm$^3$ 3-neck flask equipped with a mechanical stirrer, a thermometer, a condenser, a dropping funnel and a nitrogen inlet tube.

51 g (0.2 M) of the chloride of (dimethylvinylsilylmethoxy)-benzoic acid, previously heated to about 50° C., are run, over the course of 1 hour, into the pasty suspension thus obtained, which is kept at about 5° to 10° C.

The suspension dissolves gradually.

The brown reaction solution is kept at ambient temperature, whilst stirring, for a further 2 hours. The reaction mixture is then precipitated in 1.5 l of vigorously stirred iced water. The beige precipitate is filtered off and then washed with water.

On dissolving the cake in hot dimethylformamide, filtering hot and then cooling the filtrate, 74 g of light beige crystalline product are obtained.

The product thus prepared has a melting point of 315° C. Its infra-red spectrum exhibits the characteristic bands of the compound of the formula (20). Analysis by thin layer chromatography shows that this product is free from impurity. The percentage analysis for carbon, hydrogen and nitrogen gave the following results:

| | |
|---|---|
| C % = | 70.19 |
| H % = | 5.97 |
| N % = | 6.42 |

EXAMPLE 19

Preparation of the compound (21)

20 g (0.05 mol) of bis-(4-aminophenyl) terephthalate and 75 cm³ of N-methylpyrrolidone are introduced into the apparatus used in Example 8. The solution obtained is kept at 5°–10° C. whilst a solution of 25.5 g (0.1 mol) of the chloride of p-(vinyldimethylsilylmethoxy)-benzoic acid in 25 cm³ of N-methylpyrrolidone is added over the course of 1 hour. The mixture is then kept at 20° C. for 3 hours, after which 500 cm³ of cold water are added to the reaction mixture. This gives a yellow precipitate which is filtered off and then washed on the filter. Thereafter the precipitate is dissolved in hot dimethylformamide, the solution is filtered and the filtrate is then cooled to 20° C. This gives a white crystalline product which weighs 27.5 g after drying to constant weight in vacuo.

This product has a melting point of 301° C. and exhibits an infra-red spectrum which agrees with that of the compound of the formula (21). It does not contain impurities and the percentage analysis of the elements C, H and N gave the following results:

| | |
|---|---|
| C % = | 66.65 |
| H % = | 5.65 |
| N % = | 3.41 |

EXAMPLE 20

Preparation of the compound (22)

24 g (0.1 mol) of 4'-aminophenyl 4-aminobenzoate and 100 cm³ of N-methylpyrrolidone are introduced into the apparatus described in Example 18.

A suspension is obtained, which is kept at between 5° and 10° C. whilst a solution of 51 g (0.2 mol) of the chloride of p-(vinyldimethylsilylmethoxy)-benzoic acid in 50 cm³ of N-methylpyrrolidone is added thereto over the course of 1 hour. The reaction solution is kept at 20° C. for 2 hours after the end of the addition, and is then added to 800 cm³ of iced water whilst stirring. A precipitate is thus formed, which is filtered off and then washed with water on the filter. The precipitate is dissolved in hot dioxane, the solution is filtered and the filtrate is cooled to 20° C. This gives 56 g of a crystalline white product free from impurities, which has a melting point of 213° C. and of which the infra-red spectrum agrees with that of the compound of the formula (22). The percentage analysis of the elements C, H and N gave the following results:

| | |
|---|---|
| C % = | 66.59 |
| H % = | 6.18 |
| N % = | 4.04 |

EXAMPLE 21

Preparation of the compound (23)

21.6 g of p-phenylenediamine and 200 cm³ of N-methylpyrrolidone are introduced into the apparatus described in Example 18.

The solution is cooled to 5°–10° C. and a solution of 102 g of the chloride of p-(vinyldimethylsilylmethoxy)-benzoic acid in 100 cm³ of N-methylpyrrolidone is added over the course of 1 hour.

The contents of the flask are then heated to 60° C. and kept at this temperature for 1 hour.

The hot reaction solution is added to 1 l of iced water whilst stirring. A beige precipitate is obtained, which is filtered off, washed with water and then dissolved in hot dioxane.

This solution is filtered and the filtrate is then cooled to 20° C.

A white crystalline precipitate is obtained, which is filtered off and dried to constant weight. 83.5 g of a product of melting point 255° C., which is free from impurities and of which the infra-red spectrum agrees with that of the compound of the formula (23), are thus isolated.

The percentage analysis of the elements C, H and N gave the following results:

| | |
|---|---|
| C % = | 65.13 |
| H % = | 6.75 |
| N % = | 5.25 |

EXAMPLE 22

(1) Preparation of the compound of the formula (24)

19.8 g (0.1 mol) of 4,4'-diaminodiphenylmethane, 150 cm³ of chloroform and 23 g of triethylamine are introduced into the apparatus described in Example 18.

The contents of the flask are cooled to 4° C. and a solution of 53.5 g (0.2 mol) of the chloride of p-(divinylmethylsilylmethoxy)-benzoic acid in 100 cm³ of chloroform is then added over the course of 1 hour 50 minutes.

The reaction mixture is then washed three times with 60 cm³ of distilled water after which the chloroform is driven off by distillation. The residue obtained is recrystallised from absolute ethanol. This gives 60.5 g of a white product free from impurities, which melts at 142° C. and of which the nuclear magnetic resonance spectrum agrees with that of the compound of the formula (24).

The percentage analysis of this product gave the following results.

| | |
|---|---|
| C % = | 70.66 |
| H % = | 6.69 |
| N % = | 3.95 |
| Si % = | 8.31 |

EXAMPLE 23

Preparation of the thermoplastic elastomer 419 g of toluene, 108.14 g of an α,ω-dihydrogenopolydimethylsiloxane of number-average molecular weight 2,150 and of viscosity 26.5 cst, measured at 25° C., which contains 0.093 atom of hydrogen per 100 g of polysiloxane (n=28 in the formula I), and 31.7 g of 4,4'-N,N'-bis-[p-(vinyldimethylsilylmethoxy)-benzoyl]-diaminodiphenylmethane of the formula:

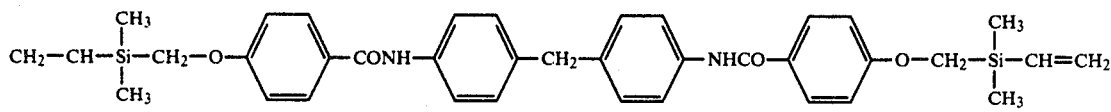

are introduced into a 1 l cylindrical glass reactor equipped with a stirring system, a heating device, a thermometer and a reflux condenser.

The contents of the reactor are stirred under a nitrogen atmosphere and then heated under reflux until a homogeneous solution is obtained. 3.3 cm$^3$ of a solution containing chloroplatinic acid (H$_2$PtCl$_6$) in isopropanol (concentration: $3 \times 10^{-6}$ gram atom of Pt/cm$^3$) are then added. An immediate increase in the viscosity of the reaction mixture is observed. The mixture is kept under these conditions for 4 hours and the toluene solution is then cooled to 20° C.

The viscosity of the solution, adjusted to 20% by weight of solids content by addition of toluene, is 30 poises at 25° C.

A film is prepared by depositing, by means of a casting machine, a uniform 0.5 mm layer of the solution of 25% solids content on a glass plate and then evaporating the solvent by heating to 80° C. for 1 hour. A transparent elastic film of 70µ thickness is obtained, the mechanical properties of which are as follows:

breaking load determined in accordance with French Standard Specification T 46,002: 88 kg/cm$^2$ elongation at break determined in accordance with French Standard Specification T 46,007: 660%.

A sample of the film obtained above is dissolved in chloroform at a concentration of 0.5 g/100 cm$^3$. The inherent viscosity of this solution, measured at 25° C., is 65 cm$^3$/g.

The examination, by infra-red spectrometry, of the product obtained makes it possible to establish the absence of a band at 10.5µ which corresponds to the ≡Si—CH=CH$_2$ group and the presence of the following bands:

3.05µ, corresponding to the —NH—group 6.10µ, corresponding to the —C—group and
$\parallel$
O 6.64µ, corresponding to the $\underset{\diagdown\diagup}{-C-NH}$ chain unit.

Furthermore, it was not possible to determine the active hydrogen by gasometric methods after treating the product with potash.

The polymer obtained above has a softening point of 160° C. and a weight-average molecular weight Mw of 170,000, measured by light-scattering on a solution in ethyl acetate; it corresponds to the structure

EXAMPLE 24

A thermoplastic elastomer of the same structure as in Example 23 is prepared by following the same procedure but replacing the toluene by 476 cm$^3$ of butyl acetate. The total duration of the reaction is 5 hours.

The solution obtained, diluted to 20% by weight of solids by addition of butyl acetate, has a viscosity of 2 poises at 25° C.

The inherent viscosity of a sample of the reaction product measured on a solution of 0.5 g in 100 cm$^3$ of chloroform at 25° C. is 53 cm$^3$/g.

The polymer thus obtained has a softening point of 160° C. The breaking load and the elongation measured as in Example 1 are respectively 68 kg/cm$^2$ and 600%.

The percentage analysis and the infra-red spectrum correspond to the product of Example 23.

EXAMPLE 25

Preparation of the thermoplastic elastomer with recurring units

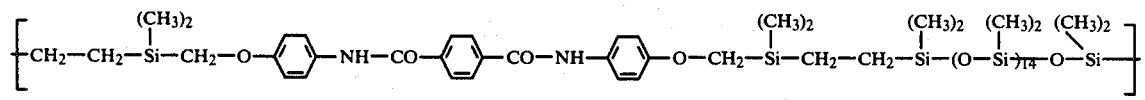

4.088 g of N,N'-bis-[p-(vinyldimethylsilylmethoxy)-phenyl]-terephthalamide, 8.36 g of an α,ω-dihydrogenopolydimethylsiloxane of number-average molecular weight 1,114, containing 0.181 atom of active hydrogen per 100 g of polymer, having a viscosity of 9.3 cst at 25° C., and containing about 15 dimethylsiloxane units, and 43 cm$^3$ of toluene are introduced into a reactor equipped as in Example 23.

The contents of the reactor are heated to the reflux temperature and 0.36 cm$^3$ of a solution of chloroplatinic acid containing $8 \times 10^{-6}$ gram atom of Pt/cm$^3$ is then added. The terephthalamide dissolves in 7 minutes. A further 0.90 cm$^3$ of chloroplatinic acid is added and heating is continued for 5 hours 30 minutes. The solution is very viscous; cooling gives a gel which is dispersed in 200 cm$^3$ of methanol and stirred vigorously. The polymer obtained is filtered off and then re-suspended in 200 cm$^3$ of methanol. It is then filtered off and dried at 80° C. under 2 mm of mercury.

This gives a product of softening point 190° C. and of inherent viscosity 32 cm$^3$/g, measured at 25° C. on a solution of 0.5 g in 100 cm$^3$ of CHCl$_3$.

The percentage composition and the infra-red spectrum correspond to those of a polymer having the recurring unit mentioned above. It was not possible to demonstrate the presence of active hydrogen which can be determined by gasometric methods after treating the

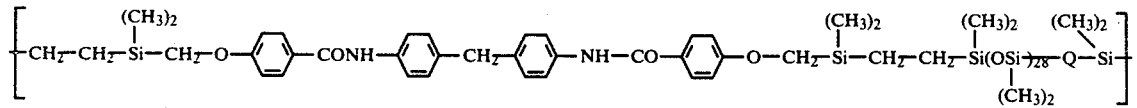

product obtained with potash. The infra-red spectrum of the product no longer contains the bands characteristic of the vinylsilyl group.

A sample is moulded by using the following procedure:

10 g of the polymer obtained above are introduced

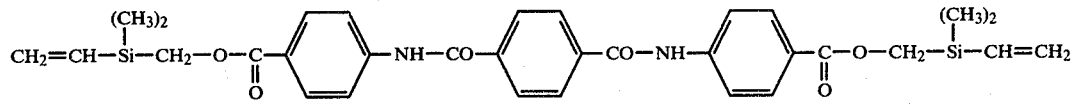

into a square mould of size 10×10×0.4 cm and the mould is placed between 2 sheets of stainless steel. The whole is placed between the platens of a press heated to 194° C., a pressure of 15 kg/cm² is then applied and the whole is kept under these conditions for 15 minutes.

After cooling, a transparent elastic sheet is obtained, the mechanical properties of which are as follows:

breaking load determined in accordance with French Standard Specification T 46,002: 141 kg/cm² elongation at break determined in accordance with French Standard Specification T 46,002: 396% tear strength in accordance with French Standard Specification T 46,007: 45 kg/cm.

EXAMPLE 26

A thermoplastic elastomeric polymer derived from N,N'-bis-[4-(vinyldimethylsilylmethoxy)-phenyl]-terephthalamide is prepared as follows:

3.17 g of N,N'-bis-[4-p-(vinyldimethylsilylmethoxy)-phenyl]-terephthalamide, 10.804 g of the α,ω-dihydrogenopolydimethylsiloxane used in Example 23, 42 g of cyclohexane and 0.3 cm³ of a solution of $H_2PtCl_6$ in toluene, containing $3.3 \times 10^{-6}$ gram atom of $Pt/cm^3$ are introduced into a reactor equipped as in Example 23 and the suspension obtained is heated to the boil. After 1 hour, an increase in the viscosity of the reaction mixture is observed; heating is continued for 7 hours 30 minutes; the reaction mixture is then in the form of a homogeneous solution. It is cooled to 20° C. and the precipitation of a polymer swollen with solvent is observed. The cooled mass is heated to 80° C. to cause the polymer to dissolve, and a film is then prepared as in Example 23 by casting the solution on a plate heated to 80° C.

This gives a film of which the inherent viscosity at 25° C., measured on a solution of 0.5 g in 100 cm³ of chloroform, is 36 cm³/g.

Its percentage composition and its infra-red spectrum correspond to those of a polymer having the recurring unit:

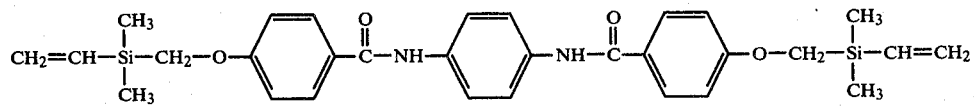

The film obtained above has the following mechanical properties (measured as in Example 23):
breaking load: 48 kg/cm²
elongation at break: 275%

EXAMPLE 27

Preparation of a thermoplastic elastomer derived from the N,N'-bis-[p-(vinyldimethylsilylmethoxycarbonyl)-phenyl]-terephthalamide of the formula:

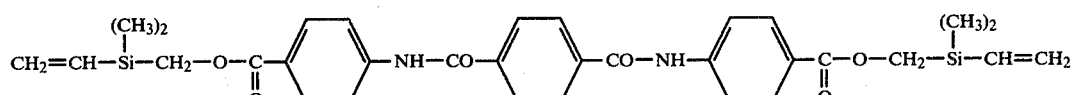

1.5 g of terephthalamide and 7.1 g of an α,ω-dihydrogenopolydimethylsiloxane of number-average molecular weight 2,930, containing 0.068 atom of active hydrogen per 100 g of polymer, of viscosity 48 cst at 20° C., and containing about 30 dimethylsiloxane units, are introduced into an apparatus equipped as in Example 23.

The contents of the flask are heated to 110° C. and 0.3 cm³ of a solution of hexachloroplatinic acid in toluene, containing $8 \times 10^{-6}$ gram atom of platinum per cm³ is added, followed by an additional quantity of chloroplatinic acid ($1.9 \times 10^{-5}$ gram atom of platinum). Heating is continued for 24 hours at 110° C. and the solution is then cooled and poured into 2 l of methanol, with vigorous stirring.

The precipitate is washed with 100 cm³ of methanol and then dried for 24 hours at 80° C. under reduced pressure (3 mm of mercury).

The inherent viscosity of the polymer measured at 25° C. on a solution of 0.5 g in 100 cm³ of chloroform is 30 cm³/g. Its softening point is 120° C.

EXAMPLE 28

Preparation of the thermoplastic elastomer 67.47 g of toluene, 15.06 g of an α,ω-dihydrogenopolydimethylsiloxane of number-average molecular weight 1,100 (n=about 13 in the formula I) and 7.42 g of 4,4'-N,N'-bis-[p-(vinyldimethylsilylmethoxy)-benzoyl]-diaminobenzene of the formula

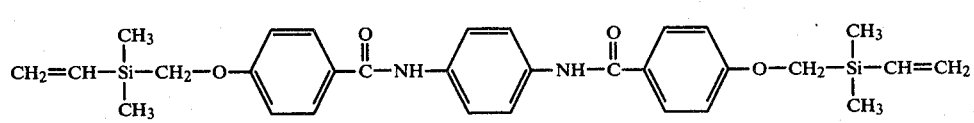

are introduced into a 250 cm³ flask equipped with a stirring system, a thermometer, a reflux condenser and a heating device.

The suspension is heated under reflux whilst stirring and 0.8 cm³ of a solution of chloroplatinic acid in toluene containing $3 \times 10^{-6}$ gram atom of platinum per cm³ is then added. The reaction mixture becomes viscous and homogeneous. It is kept under reflux for 6 hours 15 minutes.

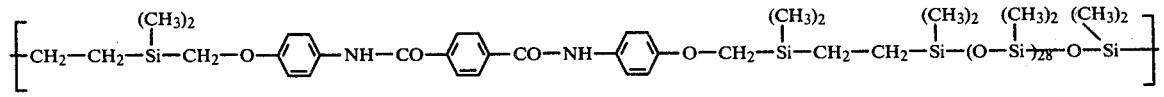

Following the procedure of Example 23, a film is prepared from the reaction solution. A white elastomer is thus obtained, having a softening point of 190° C. and an inherent viscosity of 40 cm$^3$/g, measured at 20° C. on a solution containing 0.5 g in 100 cm$^3$ of chloroform.

The percentage composition and the infra-red spectrum correspond to those of a polymer containing a plurality of recurring units of the formula:

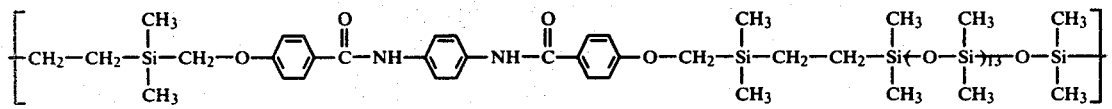

EXAMPLE 29

Preparation of the thermoplastic elastomer with recurring unit

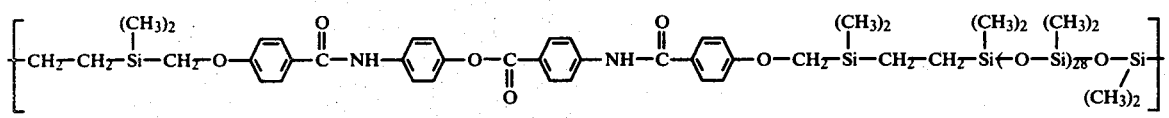

40.11 g of dioxane, 10.21 g of an α,ω-dihydrogenopolydimethylsiloxane of number-average molecular weight 2,150, used in Example 28, and 3.15 g of N-[p-(vinyldimethylsilylmethoxy)-benzoyl]-p-aminophenyl N'-[p-(vinyldimethylsilylmethoxy)-benzoyl]-p-aminobenzoate are introduced into the apparatus described in Example 28.

The contents of the flask are heated to the reflux temperature whilst stirring and 3 cm$^3$ of the catalyst solution used in Example 28 are then added.

The mixture is kept under these conditions for 5 hours 30 minutes. A film is prepared from the reaction solution. This gives a white elastomer having a softening point of 160° C. and having an inherent viscosity of 25 cm$^3$/g, measured as in Example 28.

The percentage composition and the infra-red spectrum correspond to those of the polymer having the above recurring unit.

EXAMPLES 30 to 33

Following the procedure of Example 23, a series of thermoplastic elastomers is prepared by polyaddition of the 4,4'-N,N'-bis-[p-(vinyldimethylsilylmethoxy)-benzoyl]-diaminodiphenylmethane, used in Example 23, with a series of α,ω-dihydrogenopolydimethylsiloxanes of varying number-average molecular weight; the elastomers obtained contain a plurality of recurring units analogous to that indicated in Example 23.

Films are prepared from the polymers thus obtained, in accordance with the process described in Example 23, and the mechanical properties and inherent viscosity are determined on these films. The results have been listed in the table which follows:

| EXAMPLES | α,ω-Dihydrogeno-polydimethylsiloxane | | Elastomers | | |
|---|---|---|---|---|---|
| | Mn | n | $v_{inh}$ in cm$^3$/g | breaking load in kg/cm$^2$ | elongation at break in % |
| 30 | 1,430 | 17.5 | 64 | 115 | 600 |
| 31 | 1,820 | 22.7 | 66 | 88 | 690 |
| 32 | 2,420 | 31 | 68 | 56 | 730 |
| 33 | 2,800 | 36 | 77 | 46 | 720 |

We claim:

1. A thermoplastic polysiloxane elastomer which possesses a plurality of recurring units of the general formula:

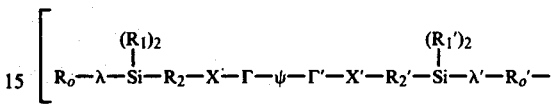

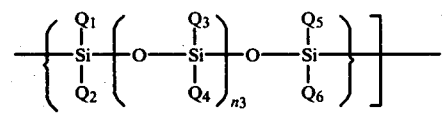

in which each of $R_o$ and $R'_o$, which may be identical or different, represents a divalent organic radical containing from 2 to 10 carbon atoms, each of λ and λ', which may be identical or different, represents a valency bond or one of the following organosilicon groups:

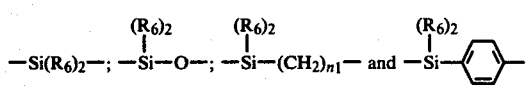

wherein each $R_6$ radical which may be identical or different, represents a methyl radical or a phenyl radical, and $n_1$ is 1, 2 or 3; each of $Q_1$ to $Q_6$, which may be identical or different, represents a linear or branched alkyl radical optionally substituted by one or more halogen atoms or cyano groups, or an aryl or alkylaryl radical, optionally substituted by one or more halogen atoms; $n_3$ is a number from 0 to 2,000 and each of $R_1$ and $R_1'$, which may be identical or different, is a straight or branched alkyl radical optionally substituted by one or more halogen atoms or cyano groups, or an aryl or alkylaryl radical, optionally substituted by one or more halogen atoms; each of $R_2$ and $R_2'$, which may be identical or different, is a straight or branched alkylene or alkylidene radical having from 1 to 4 carbon atoms; each of X and X', which may be identical or different, is a divalent radical consisting of, or containing, at least one hetero-atom selected from O, S and N, the radicals X and X' being linked to the radicals $R_2$ and $R_2'$ via the hetero-atom; each of Γ and Γ', which may be identical or different, is an organic radical having 1 to 30 carbon atoms, selected from:

(a) a divalent radical identified by —G— and —G'— and (b) a trivalent radical identified by $$-G_1\!\!\diagup \quad \text{and} \quad G_1'\!\!\diagup$$

Ψ is an organic radical selected from:

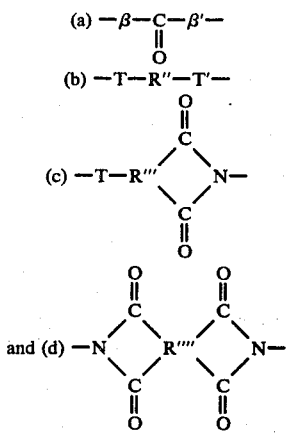

(V)
(VI)
(VII)
(VIII)

in which
each of β and β' independently represents an oxygen or nitrogen atom;
R" represents a valency bond or a divalent organic radical;
R'" represents a trivalent organic radical;
R"" represents a tetravalent organic radical and
each of T and T', which may be identical or different, represents a functional group selected from:

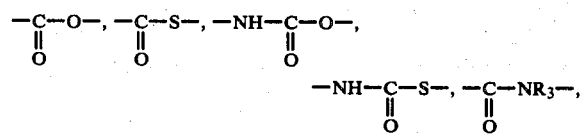

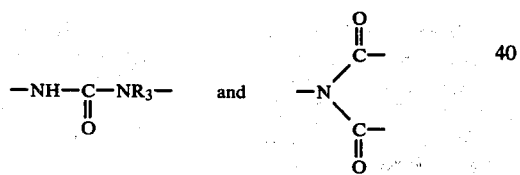

wherein $R_3$ represents a hydrogen atom or an alkyl radical having from 1 to 6 carbon atoms.

2. A thermoplastic elastomer according to claim 1 in which Ψ represents —NHCO—R"—CONH— or —CONH—R"—NHCO—.

3. A thermoplastic elastomer according to claim 1 in which $R_2$ and $R_2'$ represent a methylene radical.

4. A thermoplastic elastomer according to claim 1, which possesses a plurality of units of formula (XVII) in which the symbols $R_o$ and $R'_o$, $R_1$ and $R'_1$, $R_2$ and $R_2'$, X and X', Γ and Γ' and λ and λ' are respectively identical to one another.

5. A thermoplastic elastomer according to claim 1 in which $R_o$ and $R_o'$ represent a linear or branched alkylene group or a cycloalkylene group optionally substituted by 1 to 4 halogen atoms selected from chlorine and fluorine atoms.

6. A thermoplastic elastomer according to claim 5 in which $R_o$ and $R_o'$ represent linear alkylene radicals having from 2 to 6 carbon atoms.

7. A thermoplastic elastomer according to claim 6 in which $R_o$ and $R_o'$ are ethylene, 1,3-propylene, 1,4-butylene, hexamethylene, monochloroethylene or 1,2-difluoroethylene groups.

8. A thermoplastic elastomer according to claim 7 in which $R_o$ and $R_o'$ represent —CH$_2$—CH$_2$—.

9. A thermoplastic elastomer according to claim 1 in which $R_1$ and $R_1'$ and $Q_1$ to $Q_6$ represent linear or branched alkyl groups having up to 10 carbon atoms, optionally substituted by 1 to 4 halogen atoms selected from chlorine and fluorine or a cyano group, phenyl groups optionally substituted by 1 to 4 halogen atoms selected from chlorine and fluorine atoms, or alkylaryl radicals containing from 1 to 4 carbon atoms in the alkyl radical and optionally substituted by 1 to 4 halogen atoms selected from chlorine and fluorine atoms.

10. A thermoplastic elastomer according to claim 9, in which $R_1$, $R_1'$ and $Q_1$ to $Q_6$ represent alkyl radicals having at most 5 carbon atoms, or phenyl, tolyl or xylyl radicals optionally substituted by 1 to 4 halogen atoms selected from chlorine and fluorine atoms and/or a cyano group.

11. A thermoplastic elastomer according to claim 10 in which $R_1$, $R_1'$ and $Q_1$ to $Q_6$ are selected from methyl, ethyl, propyl, isopropyl, n-pentyl, chloromethyl, dichloromethyl, difluoromethyl, 3,3,3-trifluoropropyl, β-cyanoethyl-phenyl, m-chlorophenyl, 3,5-dichlorophenyl, o-tolyl, p-tolyl, 2,3-dimethylphenyl and 3,4-dimethylphenyl.

12. A thermoplastic elastomer according to claim 11 in which $R_1$ and $R_1'$ represent a methyl radical.

13. A thermoplastic elastomer according to claim 1 in which λ and λ' represent a valency bond.

14. A thermoplastic elastomer according to claim 1 in which X and X' represent the following functional groups:

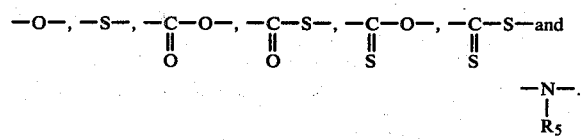

15. A thermoplastic elastomer according to claim 14 in which X and X' represent —O—.

16. A thermoplastic elastomer according to claim 1 in which Γ and Γ' represent a radical selected from
(1) divalent radicals (G and G') selected from a linear or branched alkylene radical, an alkylidene radical or a cycloalkylene radical, optionally substituted by one or more chlorine atoms, a monocyclic or polycyclic arylene radical optionally substituted by one or more methyl radicals and/or several chlorine atoms, a saturated or unsaturated or aromatic monocyclic or polycyclic heterocyclic radical containing at least one O, N and S atom, optionally substituted by one or more methyl radicals or a chain of alkylene and/or alkylidene and/or cycloalkylene and/or arylene and/or divalent heterocyclic radicals linked to one another by a valency bond and/or by at least one group selected from:

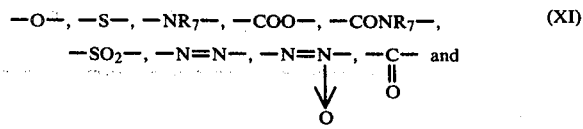

(XI)

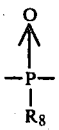

wherein each of R₇ and R₈ independently represents an alkyl radical having from 1 to 4 carbon atoms, a cyclohexyl radical or a phenyl radical and R₇ can also represent a hydrogen atom, and/or by an alkylene or alkylidene group having from 1 to 4 carbon atoms, (2) trivalent radicals (G₁ and G₁') selected from a benzenetriyl radical, a naphthalenetriyl radical or a radical of the formula

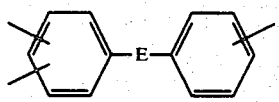 (XII)

in which E represents a valency bond or an alkylene or alkylidene group having from 1 to 4 carbon atoms, an oxygen atom, a sulphur atom or one of the groups:

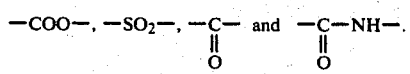

17. A thermoplastic elastomer according to claim 16, in which G and G' represent:
   (a) An alkylene or alkylidene radical having from 1 to 12 carbon atoms or a cycloalkylene radical having from 5 to 8 carbon atoms;
   (b) a phenylene, tolylene, xylylene, naphthylene or anthracenylene radical;
   (c) a saturated or unsaturated or aromatic heterocyclic radical containing at least one O, N or S atom and 4 to 6 atoms in the ring; or
   (d) a divalent radical consisting of a chain of 2 to 4 radicals as defined under (a) and/or (b) and/or (c) linked to one another by a valency bond and/or by at least one of the groups:

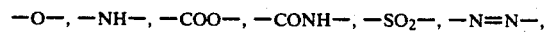

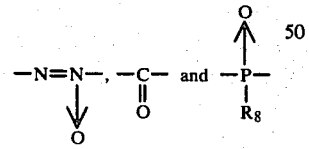

and/or by an alkylene and/or alkylidene group having from 1 to 4 carbon atoms.

18. A thermoplastic elastomer according to claim 17, in which G and G' represent an alkylene or alkylidene radical having from 1 to 6 carbon atoms, a cyclohexylene radical, a m- or p-phenylene radical, a 1,2-dimethyl-3,6-phenylene radical, a 2-methyl-1,4-phenylene radical, a 5-methyl-1,3-phenylene radical or a radical formed by two phenylene groups linked to one another by a valency bond, an alkylene or alkylidene group having from 1 to 4 carbon atoms, an oxygen atom or one of the groups

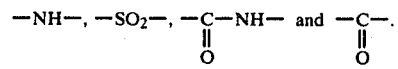

19. A thermoplastic elastomer according to claim 18 in which G and G' represent a

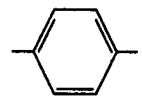

radical.

20. A thermoplastic elastomer according to claim 1, in which the trivalent groups G₁ and G₁' represent 1,2,4-benzenetriyl radicals or a radical of the formulae:

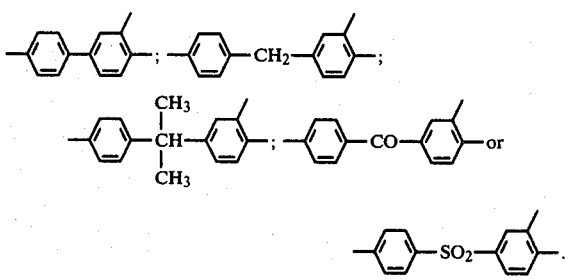

21. A thermoplastic elastomer according to claim 1, in which Ψ represents a divalent group of the formula:

—T—R''—T'— (IV)

in which R'' represents:
(1) a linear or branched alkylene radical, an alkylidene radical, a cycloalkylene radical or a monocyclic or polycyclic arylene radical optionally substituted by one or more alkyl radicals having from 1 to 4 carbon atoms and/or by one or two functional groups selected from cyano, amide, nitro, ester, alkoxy, hydroxyl, amine and hydroxycarbonyl, and/or by one or more halogen atoms;
(2) a saturated or unsaturated or aromatic monocylic or polycyclic divalent heterocyclic radical which contains at least one O, N or S atom and optionally substituted by one or more methyl radicals; or
(3) a chain of alkylene and/or alkylidene and/or cycloalkylene and/or arylene and/or divalent heterocyclic radicals linked to one another by a valency bond and/or an oxygen atom and/or a sulphur atom and/or at least one of the groups:

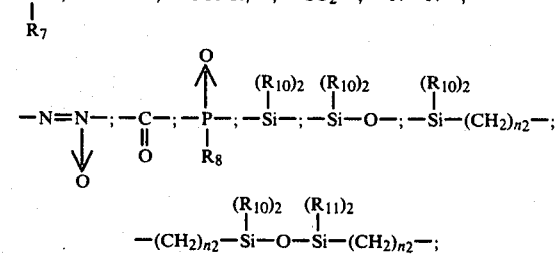

-continued

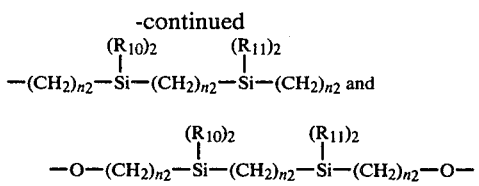

wherein each of $R_7$ and $R_8$ independently represents an alkyl radical having from 1 to 4 carbon atoms, a cyclohexyl radical or a phenyl radical and $R_7$ can also represent a hydrogen atom, n is 1, 2 or 3 and each of $R_{10}$ and $R_{11}$ independently represents a methyl or phenyl radical, and/or by an alkylene or alkylidene radical having from 1 to 4 carbon atoms.

22. A thermoplastic elastomer according to claim 21, in which Ψ represents a group of the formula (VI) in which R″ represents a radical selected from:
   (a) an alkylene or alkylidene radical having at most 12 carbon atoms or a cycloalkylene radical having from 5 to 8 carbon atoms;
   (b) a phenylene, tolylene, xylylene, naphthylene or anthracenylene radical optionally substituted by one or more chlorine atoms;
   (c) a saturated or unsaturated or aromatic heterocyclic radical containing one or two hetero atoms selected from nitrogen, sulphur and oxygen and containing 4 to 6 atoms in the ring, and optionally substituted by one or two methyl groups; and
   (d) a divalent radical consisting of a chain of 2 to 4 radicals as defined under (a) and/or (b) and/or (c) and linked to one another by a valency bond and/or by at least one of the groups:

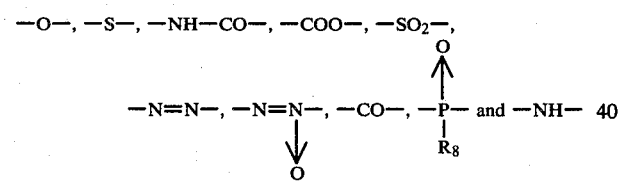

and/or by an alkylene or alkylidene radical containing from 1 to 4 carbon atoms.

23. A thermoplastic elastomer according to claim 22, in which Ψ represents a group of the formula (VI), wherein R″ is an alkylene group having from 1 to 8 carbon atoms, a cyclohexylene radical, a p-phenylene radical, a radical containing from 2 to 4 phenyl groups linked by a valency bond and/or by the groups:

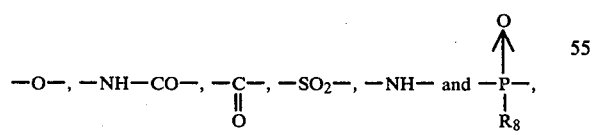

and/or by a methylene and/or isopropylidene group, or a radical containing two alkylene groups having from 1 to 4 carbon atoms, linked to a benzene ring by a valency bond and/or by the groups

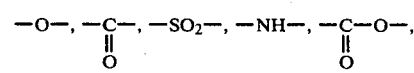

-continued

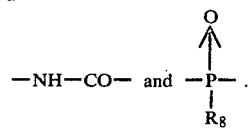

24. A thermoplastic elastomer according to claim 23 in which R″ represents a

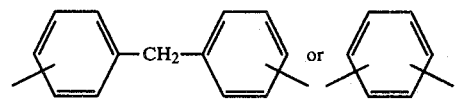

radical.

25. A thermoplastic elastomer according to claim 1, in which Ψ represents a group of the formula:

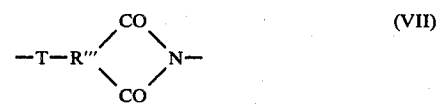 (VII)

in which R‴ represents a radical selected from:
   a saturated aliphatic hydrocarbon radical having from 2 to 20 carbon atoms,
   a saturated cycloaliphatic hydrocarbon radical containing 5 or 6 carbon atoms in the ring,
   a saturated or unsaturated or aromatic heterocyclic radical containing at least one O, N or S atom and from 4 to 6 atoms in the ring, and
   an aromatic monocyclic or a polycyclic radical in which the rings are fused or linked to one another by a valency bond and/or by an alkylene or alkylidene radical having from 1 to 4 carbon atoms and/or by at least one radical of the formula:

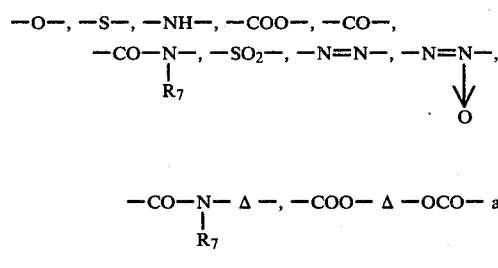

in which each of $R_7$ and $R_8$ independently represents an alkyl radical having from 1 to 4 carbon atoms, a cyclohexyl radical or a phenyl radical and $R_7$ can also represent a hydrogen atom, Δ is an alkylene radical having at most 12 carbon atoms, a cycloalkylene radical having 5 or 6 carbon atoms or an arylene radical, the aromatic rings optionally being substituted by one or more chlorine atoms and/or methyl groups.

26. A thermoplastic elastomer according to claim 25, in which Ψ represents a group of the formula:

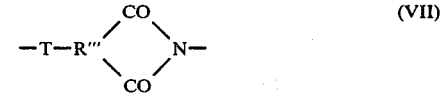 (VII)

wherein R''' represents a cyclohexanetriyl radical, a benzenetriyl radical or a radical selected from:

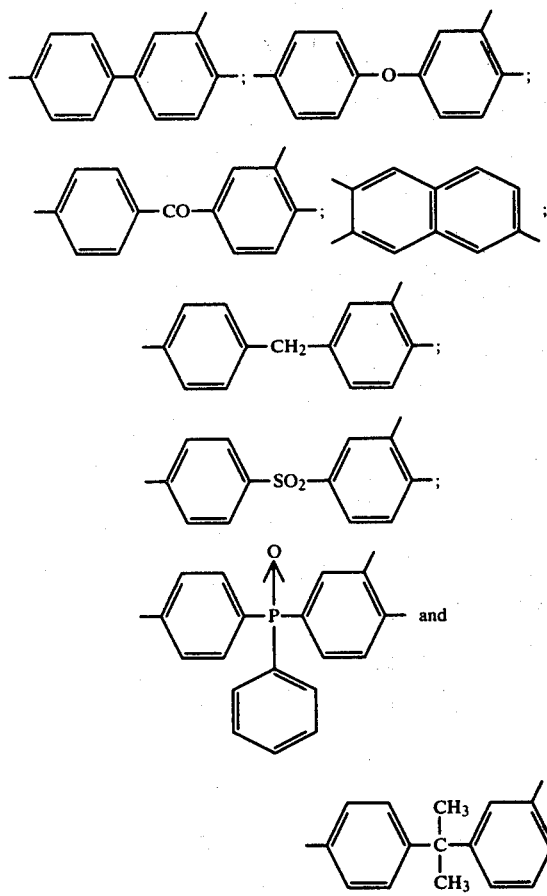

27. A thermoplastic elastomer according to claim 26, wherein R''' represents a 1,2,4-benzenetriyl radical.

28. A thermoplastic elastomer according to claim 25, in which Ψ represents a group of the formula:

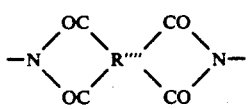
(VIII)

in which R'''' represents a radical selected from:
- a saturated aliphatic hydrocarbon radical having from 2 to 20 carbon atoms,
- a saturated cycloaliphatic hydrocarbon radical having from 5 to 6 carbon atoms,
- a saturated or unsaturated or aromatic heterocyclic radical containing at least one O, N or S atom and from 4 to 6 atoms in the ring, and
- an aromatic monocyclic, or polycyclic radical in which the rings are fused or linked to one another by a valency bond and/or by an alkylene or alkylidene radical having from 1 to 4 carbon atoms and/or by at least one radical of the formula:

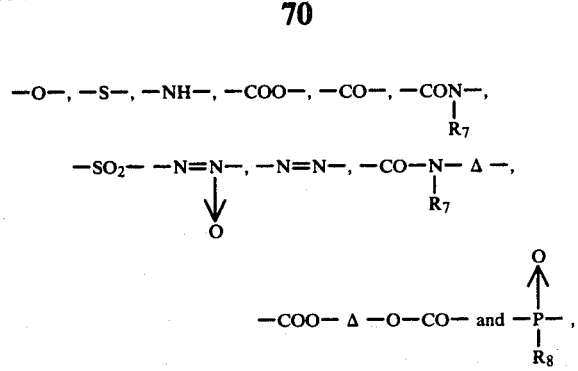

the aromatic rings optionally being substituted by one or more chlorine atoms and/or methyl groups.

29. A thermoplastic elastomer according to claim 28, in which Ψ represents a group of the formula:

$$\begin{matrix} & OC & & CO & \\ -N & & R'''' & & N- \\ & OC & & CO & \end{matrix}$$ (VIII)

in which R'''' represents a 1,2,4,5-cyclohexanetetrayl radical, a 1,2,4,5-benzenetetrayl radical or a radical selected from:

30. A thermoplastic elastomer according to claim 1, in which n₃ is a number from 10 to 200.

31. A thermoplastic elastomer according to claim 30, in which n₃ is a number from 10 to 80.

32. A thermoplastic elastomer according to claim 1, in which T and T' represent the groups:

—COO—, —CONH—, —NH—COO—,

—NH—CO—NH— or —N(CO—)(CO—)

33. A thermoplastic elastomer according to claim 1, which contains a plurality of units of the formula:

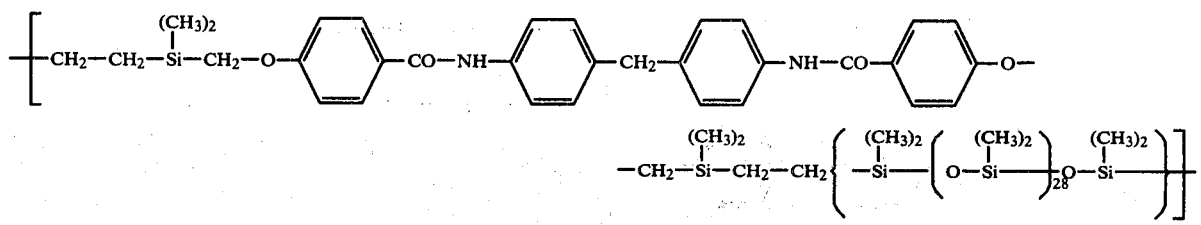

34. A thermoplastic elastomer according to claim 1, which contains a plurality of units of the formula:

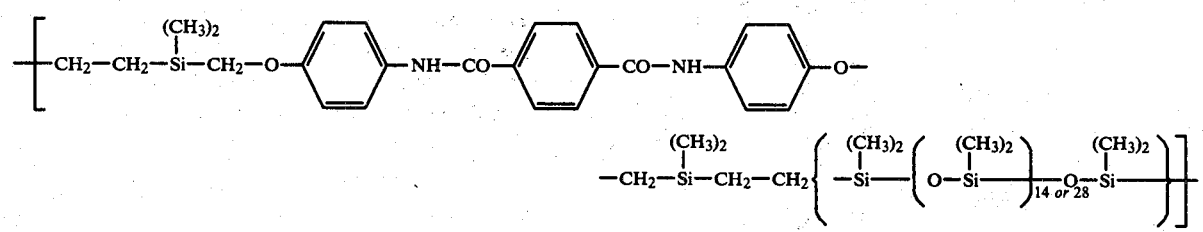

35. A thermoplastic elastomer according to claim 1, which contains a plurality of recurring units of the formula:

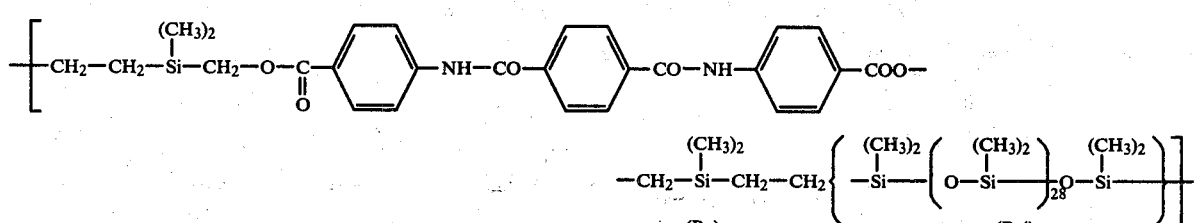

36. A thermoplastic elastomer according to claim 1, which contains a plurality of recurring units of formula:

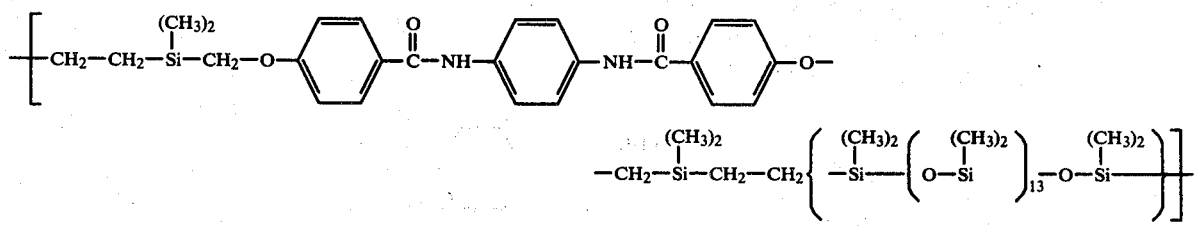

37. A thermoplastic elastomer according to claim 1, which contains a plurality of recurring units of the formula:

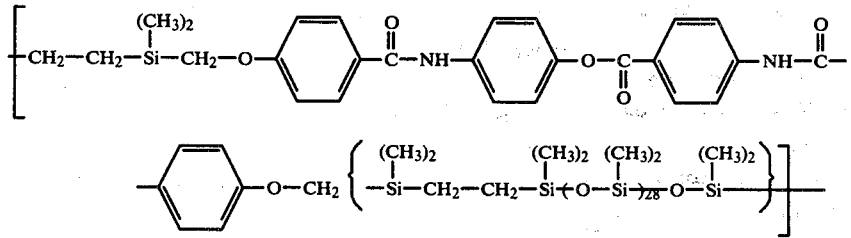

38. Process for the preparation of a thermoplastic elastomer as defined in claim 1 which comprises reacting at least one diethylenic silicon compound of the general formula:

(XVIII)

$$R-\lambda-\overset{(R_1)_2}{\underset{|}{Si}}-R_2-X-\Gamma-\psi-\Gamma'-X'-R_2'-\overset{(R_1')_2}{\underset{|}{Si}}-\lambda'-R'$$

with at least one α,ω-dihydrogenopolysiloxane of the general formula:

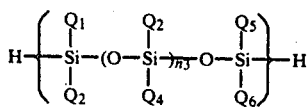

optionally in the presence of a catalyst for the hydrosilylation of ethylenic double bonds.

39. Process according to claim 38, in which R and R' are linear or branched alkenyl radicals optionally substituted by one or more halogen atoms, or cycloalkenyl radicals optionally substituted by one or more halogen atoms.

40. Process according to claim 39, in which R and R' are linear alkenyl radicals having from 2 to 6 carbon atoms.

41. Process according to claim 40, in which R and R' are linear alkenyl radicals with a terminal ethylenic double bond.

42. Process according to claim 41, in which R and R' are identical.

43. Process according to claim 39, in which R and R' are vinyl, allyl, prop-2-en-1-yl, but-3-en-1-yl, pent-4-en-1-yl or hex-5-en-1-yl groups.

44. Process according to claim 39, which is carried out at a temperature of from 0° to 300° C. and at a pressure below, above or equal to atmospheric pressure.

45. Process according to claim 39, which is carried out in the presence of an initiator of free radicals.

46. Process according to claim 39, which is carried out in the presence of a metal of group VIII or a derivative thereof, as catalyst.

47. Process according to claim 46, in which the metal is selected from Pt, Ru, Rh, Pd and Ir.

48. Process according to claim 47, in which the catalyst is selected from elementary platinum deposited on a support, hexachloroplatinic acid, an alkali metal salt thereof and a reaction product thereof with an alcohol, ether, aldehyde or cyclopropane and a complex of a platinum halide with a phosphine.

49. Process according to claim 39, which is carried out in solution or in suspension in an organic solvent which is inert towards the reactants, selected from saturated aliphatic and cycloaliphatic hydrocarbons, aromatic hydrocarbons optionally substituted by halogen atoms, alcohols, ethers and esters.

50. Process according to claim 39, in which the relative amounts of the reactants (XVIII) and (XIX) expressed in terms of the ratio of the number of alkenyl groups to the number of active hydrogen atoms is from 2 to 0.5.

51. Process according to claim 50, in which the ratio of alkenyl groups to active hydrogen is from 1.2 to 0.8.

52. Process according to claim 39, in which the reaction is carried out in the presence of at least one chain stopper selected from silicon compounds containing a single hydrogen atom linked to silicon, silicon compounds containing a single alkenyl group and monoethylenic organic compounds.

53. Process according to claim 46, in which the amount of metallic catalyst, expressed as the number of gram atoms of metal per alkenyl group present in the compound (XVIII) is from $10^{-6}$ to $10^{-1}$.

54. Process according to claim 39, in which 4,4'-N,N'-bis-[p-(vinylidimethylsilylmethoxy)-benzoyl]-diaminodiphenylmethane is reacted with an α,ω-dihydrogenopolydimethylsiloxane of number-average molecular weight 2,150 and of viscosity 26.5 cst at 25° C., in the presence of chloroplatinic acid in toluene or butyl acetate.

55. Process according to claim 39, in which N,N'-bis-[p-(vinyldimethylsilylmethoxy)-phenyl]-terephthalamide is reacted with an α,ω-dihydrogenopolydimethylsiloxane of number-average molecular weight 1,114 and of viscosity 9.3 cst at 25° C. in the presence of chloroplatinic acid in toluene.

56. Process according to claim 39, in which N,N'-bis-[p-(vinyldimethylsilylmethoxy)-phenyl]-terephthalamide is reacted with an α,ω-dihydrogenopolydimethylsiloxane of number-average molecular weight 2,150 and of viscosity 26.5 cst at 25° C. in the presence of chloroplatinic acid and in cyclohexane.

57. Process according to claim 39, in which N,N'-bis-[p-(vinyldimethylsilylmethoxycarbonyl)-phenyl]-terephthalamide is reacted with an α,ω-dihydrogenopolydimethylsiloxane of number-average molecular weight 2,930 and viscosity 48 cst at 20° C.

* * * * *